US009829488B2

(12) United States Patent
Derda et al.

(10) Patent No.: US 9,829,488 B2
(45) Date of Patent: Nov. 28, 2017

(54) PAPER-BASED CELLULAR ARRAYS

(75) Inventors: Ratmir Derda, Cambridge, MA (US); Anna Laromaine Sague, Cambridge, MA (US); George M. Whitesides, Newton, MA (US)

(73) Assignee: President and Fellows of Havard College, Cambridge, MA (US)

( * ) Notice: Subject to any disclaimer, the term of this patent is extended or adjusted under 35 U.S.C. 154(b) by 1740 days.

(21) Appl. No.: 12/934,192

(22) PCT Filed: Mar. 27, 2009

(86) PCT No.: PCT/US2009/038566
§ 371 (c)(1),
(2), (4) Date: Dec. 14, 2010

(87) PCT Pub. No.: WO2009/120963
PCT Pub. Date: Oct. 1, 2009

(65) Prior Publication Data
US 2011/0105360 A1    May 5, 2011

Related U.S. Application Data

(60) Provisional application No. 61/040,010, filed on Mar. 27, 2008, provisional application No. 61/040,030, (Continued)

(51) Int. Cl.
*G01N 33/548* (2006.01)
*B01L 3/00* (2006.01)
(Continued)

(52) U.S. Cl.
CPC ........ *G01N 33/548* (2013.01); *B01J 19/0046* (2013.01); *B01L 3/5085* (2013.01);
(Continued)

(58) Field of Classification Search
CPC . G01N 33/548; G01N 33/502; B01J 19/0046; B01J 2219/00743;
(Continued)

(56) References Cited

U.S. PATENT DOCUMENTS 4,618,475 A    10/1986  Wang
4,668,564 A    5/1987   Orchard
(Continued)

FOREIGN PATENT DOCUMENTS

CN    1586636 A    3/2005
JP    08233799 A   9/1996
(Continued)

OTHER PUBLICATIONS

Merriam-Webster's Collegiate Dictionary, Eleventh Edition, "Jojoba" Definition.*
(Continued)

*Primary Examiner* — Jeremy C Flinders
(74) *Attorney, Agent, or Firm* — Wilmer Cutler Pickering Hale and Dorr LLP

(57) ABSTRACT

Three-dimensional cellular arrays, methods of making three-dimensional cellular arrays, and methods of identifying agents using the arrays are disclosed.

20 Claims, 27 Drawing Sheets

Related U.S. Application Data filed on Mar. 27, 2008, provisional application No. 61/097,718, filed on Sep. 17, 2008, provisional application No. 61/146,413, filed on Jan. 22, 2009.

(51) Int. Cl.
  *B01J 19/00* (2006.01)
  *G01N 33/50* (2006.01)

(52) U.S. Cl.
  CPC ............... *B01J 2219/00527* (2013.01); *B01J 2219/00605* (2013.01); *B01J 2219/00619* (2013.01); *B01J 2219/00641* (2013.01); *B01J 2219/00644* (2013.01); *B01J 2219/00743* (2013.01); *B01L 2300/0819* (2013.01); *B01L 2300/0829* (2013.01); *B01L 2300/126* (2013.01); *B01L 2300/161* (2013.01); *G01N 33/502* (2013.01)

(58) Field of Classification Search
  CPC .... B01J 2219/00641; B01J 2219/00619; B01J 2219/00527; B01J 2219/00644; B01L 3/5085; B01L 2300/0829; B01L 2300/0819; B01L 2300/161; B01L 2300/126
  See application file for complete search history.

(56) References Cited

U.S. PATENT DOCUMENTS

| | | | |
|---|---|---|---|
| 4,668,619 A | 5/1987 | Greenquist et al. | |
| 4,743,530 A | 5/1988 | Farid et al. | |
| 4,757,004 A | 7/1988 | Houts et al. | |
| 4,861,711 A | 8/1989 | Friesen et al. | |
| 5,120,544 A | 6/1992 | Henley | |
| 5,209,904 A | 5/1993 | Forney et al. | |
| 5,266,179 A | 11/1993 | Nankai et al. | |
| 5,279,944 A | 1/1994 | Fabrizi et al. | |
| 5,409,664 A | 4/1995 | Allen | |
| 5,648,252 A | 7/1997 | Dumitriu et al. | |
| 5,707,818 A | 1/1998 | Chudzik et al. | |
| 5,834,226 A | 11/1998 | Maupin | |
| 5,858,392 A | 1/1999 | Dumitriu et al. | |
| 5,869,172 A | 2/1999 | Caldwell | |
| 5,897,522 A | 4/1999 | Nitzan | |
| 5,906,934 A | 5/1999 | Grande et al. | |
| 5,925,259 A | 7/1999 | Biebuyck et al. | |
| 5,941,862 A | 8/1999 | Haynes et al. | |
| 6,004,442 A | 12/1999 | Choulga et al. | |
| 6,025,203 A | 2/2000 | Vetter et al. | |
| 6,060,534 A | 5/2000 | Ronan et al. | |
| 6,180,239 B1 | 1/2001 | Whitesides et al. | |
| 6,202,471 B1 | 3/2001 | Yadav et al. | |
| 6,210,907 B1 | 4/2001 | Cha | |
| 6,284,072 B1 | 9/2001 | Ryan et al. | |
| 6,319,310 B1 | 11/2001 | Wong et al. | |
| 6,391,523 B1 | 5/2002 | Hurditch et al. | |
| 6,416,642 B1 | 7/2002 | Alajoki et al. | |
| 6,440,645 B1 | 8/2002 | Yon-Hin et al. | |
| 6,440,725 B1 | 8/2002 | Pourahmadi et al. | |
| 6,478,938 B1 | 11/2002 | Paek et al. | |
| 6,566,575 B1 | 5/2003 | Stickels et al. | |
| 6,642,408 B2 | 11/2003 | Batlaw et al. | |
| 6,761,962 B2 | 7/2004 | Bentsen et al. | |
| 6,816,125 B2 | 11/2004 | Kuhns et al. | |
| 6,844,200 B2 | 1/2005 | Brock | |
| 6,887,701 B2 | 5/2005 | Anderson et al. | |
| 6,919,046 B2 | 7/2005 | O'Connor et al. | |
| 6,931,523 B1 | 8/2005 | Tomoson et al. | |
| 6,935,772 B2 | 8/2005 | Karp et al. | |
| 6,951,682 B1 | 10/2005 | Zebala | |
| 6,951,757 B2 | 10/2005 | Sabatini | |
| 6,989,128 B2 | 1/2006 | Alajoki et al. | |
| 7,008,799 B1 | 3/2006 | Zimmer et al. | |
| 7,063,979 B2 * | 6/2006 | MacBeath et al. | ........ 435/305.2 |
| 7,186,352 B2 | 3/2007 | Morse et al. | |
| 7,192,693 B2 | 3/2007 | Bryant | |
| 7,291,857 B2 | 11/2007 | Tanaka et al. | |
| 7,303,923 B2 | 12/2007 | Hardman et al. | |
| 2002/0034616 A1 | 3/2002 | Vanmaele et al. | |
| 2002/0187560 A1 | 12/2002 | Pezzuto et al. | |
| 2003/0032203 A1 | 2/2003 | Sabatini et al. | |
| 2003/0148401 A1 | 8/2003 | Agrawal et al. | |
| 2004/0067166 A1 | 4/2004 | Karinka et al. | |
| 2004/0103808 A1 | 6/2004 | Lochun et al. | |
| 2005/0145496 A1 | 7/2005 | Goodsaid et al. | |
| 2005/0169962 A1 | 8/2005 | Bhatia et al. | |
| 2005/0196702 A1 | 9/2005 | Bryant et al. | |
| 2005/0266582 A1 | 12/2005 | Modlin et al. | |
| 2006/0014003 A1 | 1/2006 | Libera et al. | |
| 2006/0038182 A1 | 2/2006 | Rogers et al. | |
| 2006/0088857 A1 | 4/2006 | Attiya et al. | |
| 2006/0130054 A1 | 6/2006 | Bocking et al. | |
| 2006/0226575 A1 | 10/2006 | Maghribi et al. | |
| 2006/0292690 A1 | 12/2006 | Liu et al. | |
| 2007/0179117 A1 | 8/2007 | Reiner et al. | |
| 2007/0196819 A1 | 8/2007 | Asberg et al. | |
| 2007/0224701 A1 | 9/2007 | Rosenstein | |
| 2007/0278097 A1 | 12/2007 | Bhullar et al. | |
| 2007/0298433 A1 | 12/2007 | Sia et al. | |
| 2008/0193536 A1 * | 8/2008 | Khademhosseini et al. | . 424/486 |
| 2009/0298191 A1 | 12/2009 | Whitesides et al. | |

FOREIGN PATENT DOCUMENTS

| | | |
|---|---|---|
| WO | WO-97/48257 | 12/1997 |
| WO | WO-99/46644 | 9/1999 |
| WO | WO-00/33078 | 6/2000 |
| WO | WO-03/015890 A1 | 2/2003 |
| WO | WO-2004/080138 | 9/2004 |
| WO | WO-2005/090975 | 9/2005 |
| WO | WO-2005/107938 | 11/2005 |
| WO | WO-2006/076703 | 7/2006 |
| WO | WO-2007/029250 | 3/2007 |
| WO | WO-2007/081848 | 7/2007 |
| WO | WO-2007/116056 | 10/2007 |
| WO | WO-2008/049083 | 4/2008 |
| WO | WO-2009/120963 | 10/2009 |
| WO | WO-2009/121037 A2 | 10/2009 |
| WO | WO-2009/121038 | 10/2009 |
| WO | WO-2009/121041 A2 | 10/2009 |
| WO | WO-2009/121043 A2 | 10/2009 |
| WO | WO-2010/022324 A2 | 2/2010 |
| WO | WO-2010/102279 A1 | 9/2010 |
| WO | WO-2010/102294 A1 | 9/2010 |

OTHER PUBLICATIONS

Nicodemus et al, Tissue Engineering: Part B, vol. 14, No. 2, 2008.*
Xu et al, Biomaterials 26 (2005) 93-99.*
Napolitano et al, Tissue Engineering, vol. 13, No. 8, 2007.*
Lee et al, Biomaterials 28 (2007) 2987-2993.*
Derda, et al., "Paper-supported 3D Cell Culture for Tissue-Based Bioassays," PNAS, vol. 106, No. 44, Nov. 2009, pp. 18457-18462.
Supplementary European Search Report and Written Opinion for European Application No. 09724164 dated Mar. 16, 2011, 7 pages.
Bissell, et al., "Review: The Organizing Principle: Microenvironmental Influences in the Normal and Malignant Breast," Differentiation, 2002, 70, pp. 537-546.
Costerton, et al., "Discussion: Introduction to Biofilm," International Journal of Antimicrobial Agents, 11, 1999, pp. 217-221.
Lucas, et. al., "Multiple Forms of Angiostatin Induce Apoptosis in Endothelial Cells," Blood, vol. 92, No. 12, Dec. 1998, pp. 4730-4741.
Wodarz, et al., "Cell Polarity in Development and Cancer," Nature Cell Biology, vol. 9, No. 9, Sep. 2007, pp. 1016-1024.
Yonehara, et al., "A Cell-Killing Monoclonal Antibody (Anti-Fas) to a Cell Surface Antigen Co-Downregulated with the Receptor of Tumor Necrosis Factor," J. Exp. Med., vol. 169, May 1989, pp. 1747-1756.

(56) References Cited

OTHER PUBLICATIONS

Aikio, et al., "Bioactive Paper and Fibre Products: Patent and Literary Survey," VTT Working Papers 51, VTT-Work-51, 2006, 84 pages.

Aizenberg, et al., "Calcitic Microlenses as Part of the Photoreceptor System in Brittlestars," Nature, vol. 412, Aug. 2001, pp. 819-822.

Albrecht, et al., "Probing the Role of Multicellular Organization in Three-Dimensional Microenvironments," Nature Methods, vol. 3, No. 5, May 2006, pp. 369-375.

Alon, et al., "Letters to Nature: Robustness in Bacterial Chemotaxis," Nature, vol. 397, Jan. 1999, pp. 168-171.

Anderson, et al., "Reports: Intracellular Bacterial Biofilm-Like Pods in Urinary Tract Infections," Science, vol. 301, Jul. 2003, pp. 105-107.

Asahara, et al., "Isolation of Putative Progenitor Endothelial Cells for Angiogenesis," Science, vol. 275, Issue 5302, 1997, 4 pages.

Augst, et al., "Alginate Hydrogels as Biomaterials," Macromol. Biosci., 2006, 6, pp. 623-633.

Author Unknown, "Focus: Lab on Paper, DOI: 10.1039/b814043j," Lab Chip, vol. 8, No. 12, Dec. 2008, pp. 1988-1991, XP002585318, The Royal Society of Chemistry.

Bailey, et al., "Microarrays of Small Molecules Embedded in Biodegradable Polymers for Use in Mammalian Cell-Based Screens," PNAS, vol. 101, No. 46, Nov. 2004, pp. 16144-16149.

Barbucci, et al., "$Cu^{2+}$- and $Ag^+$-complexes with a Hyaluronane-Based Hydrogel," J. Mater. Chem., 2002, 12, pp. 3084-3092.

Beech, et al., "Biocorrosion: Towards Understanding Interactions Between Biofilms and Metals," Science Direct, Current Opinion in Biotechnology, 2005, 15, pp. 181-186.

Berggren, et al., "Paper Electronics and Electronic Paper," IEEE, Section 12: Flexible Systems, 2001, pp. 300-303.

Bracher, et al., "Heterogeneous Films of Ionotropic Hydrogels Fabricated from Delivery Templates of Patterned Paper," Adv. Mater., 2008, pp. 1807-1812.

Brooks, et al., "A Simple Artificial Urine for the Growth of Urinary Pathogens," Left. Appl. Microbiol., 1997, 24, pp. 203-206.

Bruzewicz, et al., "Low-Cost Printing of Poly(dimethylsiloxane) Barriers to Define Microchannels in Paper," Anal. Chem., 2008, 80, pp. 3387-3392.

Bruzewicz, et al., "Paper: Fabrication of a Modular Tissue Construct in a Microfluidic Chip," Lab Chip, 2008, 8, pp. 663-671.

Campana, et al., "Double and Triple Staining Methods for Studying the Proliferative Activity of Human B and T Lymphoid Cells," Journal of Immunological Methods, 107, 1988, pp. 79-88.

Carrel, et al., "Cultivation in Vitro of Malignant Tumors," J. Exp. Med., 13, 1911, 6 pages.

Carrel, et al., "Cultivation of Tissues in Vitro and its Technique," J. Exp. Med., 17, 1911, 19 pages.

Carrilho, et al., "Paper Microzone Plates," Analytical Chemistry, vol. 81, No. 15, Aug. 2009, pp. 5990-5998.

Carrilho, et al., "Understanding Wax Printing: A Simple Micropatterning Process for Paper-Based Microfluidics," Analytical Chemistry, vol. 81, No. 16, Aug. 2009, pp. 7091-7095.

Chadee, et al., "Increased Phosphorylation of Histone H1 in Mouse Fibroblasts Transformed with Oncogenes or Constitutively Active Mitogen-Activated Protein Kinase Kinase," The Journal of Biological Chemistry, vol. 270, No. 34, Aug. 1995, pp. 20098-20105.

Chang, et al., "Injection Molding of Chondrocyte/Aliginate Constructs in the Shape of Facial Implants," Journal of Biomedical Materials Research, 2001, 55, pp. 503-511.

Chen, et al., "Effects of ectopic overexpression of p21 WAF1/CIP1 on aneuploidy and the malignant phenotype of human brain tumor cells," Oncogene 13, 1996, pp. 1395-1403.

Chen, et al., "Geometric Control of Cell Life and Death," Science, vol. 276, May 1997, pp. 1425-1428.

Cheng, et al., "Clinical Analytics: Paper-Based Elisa**," Agnew. Chem., 2010, 122, pp. 1-5.

Chin, et al., "Lab-on-a-chip Devices for Global Health: Past Studies and Future Opportunities," Lab Chip, 2007, 7, pp. 41-57, A Journal of The Royal Society of Chemistry.

Cohen, et al., "Direct Freeform Fabrication of Seeded Hydrogels in Arbitrary Geometries," Tissue Engineering, vol. 12, No. 5, 2006, pp. 1325-1335, 13 pages.

Costerton, et al., "Bacterial Biofilms: a Common Cause of Persistent Infections," Science Mag., 1999, pp. 1318-1322.

Cozzi, et al., "Chrom. 3456: Alginic Acid, a New Thin Layer Material, Part 1," Journal of Chromatography, 35, 1968, pp. 396-404.

Cozzi, et al., "Chrom. 3457, Thin-Layer Chromatography of Metal Ions on Alginic Acid, Part II," Journal of Chromatography, 35, 1968, pp. 405-415.

Cukierman, et al., "Taking Cell-Matrix Adhesions to the Third Dimension," Science, vol. 294 (5547), Nov. 2001, pp. 1708-1712.

Daar, et al., "Top Ten Biotechnologies for Improving Health in Developing Countries," Nature Genetics, vol. 32, Oct. 2002, pp. 229-232.

Dean, et al., "Tumour Stem Cells and Drug Resistance," Nature Reviews, Cancer, vol. 5, Apr. 2005, pp. 275-284, 11 pages.

Devreotes, "Chemotaxis in Eukaryotic Cells: a Focus on Leukocytes and Dictyostelium," Ann. Rev. Cell Biol., 1988, 4, pp. 648-686.

Ding, et al., "A Role for Chemistry in Stem Cell Biology," Nature Biotechnology, vol. 22, No. 7, Jul. 2004, pp. 833-840.

Discher, et al., "Materials and Biology Review: Tissue Cells Feel and Respond to the Stiffness of their Substrate," Science, vol. 310, Nov. 2005, pp. 1139-1143.

DiTizio, et al., "A Liposomal Hydrogel for the Prevention of Bacterial Adhesion to Catheters," Biomaterials, 19, 1998, pp. 1877-1884.

Donlan, "Biofilm Formation: A Clinically Relevant Microbiological Process," Healthcare Epidemiology, CID 2001:33, Oct. 2001, pp. 1387-1392.

Donlan, "Biofilms and Device-Associated Infections," Emerging Infectious Diseases, vol. 7 No. 2, 2001, pp. 277-281.

Donlan, "Biofilms: Microbial Life on Surfaces," Emerging Infectious Diseases, vol. 8 No. 9, 2002, pp. 881-890.

Donlan, et al., "Biofilm Formation on Cast Iron Substrata in Water Distribution Systems," Wat. Res. vol. 28, No. 6, pp. 1497-1503, 1994.

Donlan, et al., "Reviews: Biofilms: Survival Mechanisms of Clinically Relevant Microorganisms," Clinical Microbiology Reviews, vol. 15, No. 2, Apr. 2002, pp. 167-193.

Dungchai, et al., "Electrochemical Detection for Paper-Based Microfluidics," Anal. Chem., 2009, 81, pp. 5821-5826.

Ebling, "The Permanent Life of Connective Tissue Outside of the Organism," J. Exp. Med., 17, 1913, 15 pages.

Emerman et al., "Maintenance and Induction of Morphological Differentiation in Dissociated Mammary Epithelium on Floating Collegen Membranes," In Vitro, 1977, pp. 316-328.

Emerman, et al., "Hormonal Effects on Intracellular and Secreted Casein in Cultures of Mouse Mammary Epithelial Cells on Floating Collagen Membranes," Proc. Natl. Acad. Sci., vol. 74, No. 10, Oct. 1977, pp. 4466-4470.

Engelse, et al., "Original Paper: Differential Gene Expression Analysis of Tubule Forming and Non-Tubule Forming Endothelial Cells: CDC42GAP as a Counter-Regulator in Tubule Formation," Angiogenesis, 2008, 11, pp. 153-167.

Engler, et al., "Matrix Elasticity Directs Stem Cell Lineage Specification," Cell 126, Aug. 2006, pp. 677-689.

Ghosh, et al., "Tumor-Derived Endothelial Cells Exhibit Aberrant Rho-Mediated Mechanosensing and Abnormal Angiogenesis in Vitro," PNAS, Aug. 2008, vol. 105, No. 32, pp. 11305-11310.

Gombotz, et al., "Protein Release from Aliginate Matrices," Advanced Drug Delivery Reviews 31, 1998, pp. 267-285.

Gopinathan, et al., "Microbial Contamination of Hydrogel Contact Lenses," Journal of Applied Microbiology, 1997, 82, pp. 653-658.

Griffith, et al., "Capturing Complex 3D Tissue Physiology in Vitro," Nature Reviews, Molecular Cell Biology, vol. 7, Mar. 2006, pp. 211-224.

Habash, et al., "Therapeutic Review: Microbial Biofilms: Their Development and Significance for Medical Device-Related Infections," J. Clin. Pharmacol., 1999, 39, pp. 887-898.

(56) References Cited

OTHER PUBLICATIONS

Hall-Stoodley, et al., "Bacterial Biofilms: From the Natural Environment to Infectious Diseases," Nature Reviews, Microbiology, vol. 2, Feb. 2004, pp. 95-108.
Harison, et al., "Methodology Article: High-Throughput Metal Susceptibility Testing of Microbial Biofilms," Bmc Microbiology, 2005, 5:53, 11 pages.
Heilmann, et al., "Evidence for Autolysin-Mediated Primary Attachment of Staphylococcus Epidermidis to a Polystyrene Surface," Molecular Microbiology, 1997, 24(5), pp. 1013-1024.
Heilmann, et al., "Molecular Basis of Intercellular Adhesion in the Biofilm-Forming Staphylococcus Epidermidis," Molecular Microbiology, 1996, 20(5), pp. 1083-1091.
Hoshino, et al, S-Phase Fraction of Human Brain Tumors In Situ Measured by Update of Bromodeoxyuridine, Int. J. Cancer 38, 1986, pp. 369-374.
Huang et al., "Review: The Structural and Mechanical Complexity of Cell-Growth Control," Nature Cell Biology, vol. 1, Sep. 1999, pp. E131-E138.
International Search Report and Written Opinion of the International Searching Authority, the European Patent Office, for International Application No. PCT/US2007/081848, dated Jan. 28, 2009, 12 pages.
International Search Report and Written Opinion of the International Searching Authority, the European Patent Office, for PCT/US2010/026499, dated Jun. 16, 2010, 2 pages.
International Search Report and Written Opinion of the International Searching Authority, the Korean Intellectual Property Office, for International Application No. PCT/US2009/038566, dated Dec. 16, 2009, 10 pages.
International Search Report and Written Opinion of the International Searching Authority, the Korean Intellectual Property Office, for International Application No. PCT/US2009/038694 dated Nov. 12, 2009, 10 pages.
International Search Report and Written Opinion of the International Searching Authority, the Korean Intellectual Property Office, for PCT/US2009/038693, dated Oct. 28, 2009, 8 pages.
International Search Report and Written Opinion of the International Searching Authority, the Korean Intellectual Property Office, for PCT/US2009/038699, dated Oct. 28, 2009, 9 pages.
International Search Report and Written Opinion of the International Searching Authority, the Korean Intellectual Property Office, for PCT/US2009/038702, dated Nov. 11, 2009, 7 pages.
International Search Report of the International Searching Authority, the European Patent Office, for PCT/US2010/026547, dated Jul. 19, 2010, 3 pages.
International Search Report of the International Searching Authority, the Korean Intellectual Property Office, for PCT/US2009/054601, dated Mar. 22, 2010, 2 pages.
Jen, et al., "Review: Hydrogels for Cell Immobilization," Biotechnology and Bioengineering, vol. 50, 1996, pp. 357-364.
Jeoung, et al., "Effects of Tumor Necrosis Factor-a on Antimitogenicity and Cell Cycle-Related Proteins in MCF-7 Cells," The Journal of Biological Chemistry, vol. 270, No. 31, Aug. 1995, pp. 18367-18373.
Kahn, et al., "Gene Expression Profiling in an In Vitro Model of Angiogenesis," American Journal of Pathology, vol. 156, No. 6, Jun. 2000, pp. 1887-1990.
Klajn, et al., "Multicolour Micropatterning of Thin Films and Dry Gels," Nature Materials, vol. 3, Oct. 2004, pp. 729-735.
Koh, et al., "Cdc42- and Rac1-mediated Endothelial Lumen Formation Requires Pak2, Pak4 and Par3, and PKC-Dependent Signaling," Journal of Cell Science, 121(7), 2008, pp. 989-101.
Kuo, et al., "Ionically Crosslinked Alginate Hydrogels as Scaffolds for Tissue Engineering: Part 1: Structure, Gelation Rate and Mechanical Properties," Biomaterials, 22, 2001, pp. 511-521.
Lahav, et al., "DOI: 10.1002/adma.200601843—Patterning of Poly(acrylic acid) by Ionic Exchange Reactions in Microfluidic Channels**," Advanced Materials, 2006, 18, pp. 3174-3178.
Lazebnik, et al., "Cleavage of poly(ADP-ribose) Polymerase by a Proteinase with Properties like ICE," Nature, vol. 371, Sep. 1994, pp. 346-347.
Leary, et al., "Rapid and Sensitive Colorimetric Method for Visualizing Biotin-Labeled DNA Probes Hybridized to DNA or RNA Immobilized on Nitrocellulose: Bio-Blots," PNAS, vol. 80, No. 13, 1983, pp. 4045-4049.
Lee, et al., "Commentary: Cell Polarity and Cancer-Cell and Tissue Polarity as a Non-Canonical Tumor Suppressor," Journal of Cell Science, 121 (8), 2008, pp. 1141-1150.
Leighton, et al., "Contributions of Tissue Culture Studies to an Understanding of the Biology of Cancer: A Review," Cancer Research, vol. 17, No. 10, Nov. 1957, pp. 929-941.
Lewis, "Persister Cells, Dormancy and Infectious Disease," Nature Reviews, Microbiology, vol. 5, Jan. 2007, pp. 48-56.
Li, et al., "Thread as a Versatile Material for Low-Cost Microfluidic Diagnostics," Applied Materials & Interfaces, vol. 2, No. 1, Jan. 2010, 6 pages.
Lim, et al., "Microencapsulation of Living Cells and Tissues," Journal of Pharmaceutical Sciences, vol. 70, No. 4, 1981, pp. 351-351.
Lin, et al., "Hydrogels in Controlled Release Formulations: Network Design and Mathematical Modeling," ScienceDirect, Advanced Drug Delivery Reviews, 58, 2006, pp. 1379-1408.
Liu, et al., "Shape-Controlled Production of Biodegradable Calcium Alginate Gel Microparticles Using a Novel Microfluidic Device," Langmuir, 2006, 22, pp. 9453-9457.
Liu, et al., "Three-Dimensional Photopatterning of Hydrogels Containing Living Cells," Biomed. Microdevices, 2002, 4, pp. 257-266.
Lu, et al., "Short Communication: Rapid Prototyping of Paper-Based Microfluidics with Wax for Low-Cost, Portable Bioassay," Electrophoresis, 2009, 30, pp. 1497-1500.
Mabey, et al., "Diagnostics for the Developing World," Nature Reviews / Microbiology, vol. 2, Mar. 2004, pp. 231-240.
Mahadevan, et al., "Biomimetic Ratcheting Motion of a Soft, Slender, Sessile Gel," PNAS, vol. 101, No. 1, Jan. 2004, pp. 23-26.
Martinez, et al., "Diagnostics for the Developing World: Microfluidic Paper-Based Analytical Devices," Analytical Chemistry, vol. 82, No. 1, Jan. 2010, pp. 3-10.
Martinez, et al., "FLASH: A Rapid Method for Prototyping Paper-Based Microfluidic Devices," Lab Chip, 2008, 8, pp. 2146-2150, A Journal of the Royal Society of Chemistry.
Martinez, et al., "Paper: Programmable Diagnostic Devices Made from Paper and Tape," Lab Chip, Jul. 2010, 6 pages.
Martinez, et al., "Patterned Paper as a Platform for Inexpensive, Low-Volume, Portable Bioassays**," Agnew. Chem. Int. Ed., 2007, 46, pp. 1318-1320.
Martinez, et al., "Simple Telemedicine for Developing Regions: Camera Phones and Paper-Based Microfluidic Devices for Real-Time, Off-Site Diagnosis," Analytical Chemistry, vol. 80, No. 10, May 2008, pp. 3699-3707.
Martinez, et al., "Three-Dimensional Microfluidic Devices Fabricated in Layered Paper and Tape," PNAS, vol. 105, No. 50, Dec. 2008, pp. 19606-19611.
Matsumoto, et al., "Three-Dimensional Cell and Tissue Patterning in a Strained Fibrin Gel System," PLoS One, Nov. 2007, Issue No. 11, 6 pages.
McGuigan, et al., "Cell Encapsulation in Sub-mm Sized Gel Modules Using Replica Molding," PLoS One, May 2008, vol. 3, Issue 5, 11 pages.
Morrison, et al., "Insight Review: Asymmetric and Symmetric Stem-Cell Divisions in Development and Cancer," Nature, vol. 44, Jun. 2006, pp. 1068-1074.
Nelson, et al., "Of Extracellular Matrix, Scaffolds, and Signaling: Tissue Architecture Regulates Development, Homeostasis, and Cancer," Annu. Rev. Cell. Dev. Biol., 2006, 22, pp. 287-309, 25 pages.
Nelson, et al., "Three-Dimensional Lithographically Defined Organotypic Tissue Arrays for Quantitative Analysis of Morphogenesis and Neoplastic Progression," Nature Protocols, vol. 3, No. 4, 2008, pp. 674-678.
Ni, et al., "Cell morphology and migration linked to substrate rigidity," Soft Matter, 2007, pp. 1285-1292.

(56) References Cited

OTHER PUBLICATIONS

Nie et al., "Paper: Integration of Paper-based Microfluidic Devices with Commercial Electrochemical Readers," Lab Chip, Oct. 2010, 7 pages.
Paul, "The Cancer Cell in Vitro: A Review," Cancer Res., 1962, 22, pp. 431-440, 11 pages.
Peele, et al., "Semi-Automated vs. Visual Reading of Urinalysis Dipsticks," Clin. Chem, 1977, 23, pp. 2242-2246.
Pelham, et al., "Cell Biology: Cell Locomotion and Focal Adhesions are Regulated by Substrate Flexibility," Proc. Natl. Acad. Sci, vol. 94, pp. 13661-13665.
Pugia, et al., "High-Sensitivity Dye Binding Assay for Albumin in Urine," J. Clin. Lab. Anal. 1999, 13, pp. 180-187.
Reches, et al., "Thread as a Matrix for Biomedical Assays," Applied Materials & Interfaces, vol. xxx, No. xx, 000, xxxx, pp. A-G, 2010.
Reya, et al., "Stem Cells, Cancer, and Cancer Stem Cells," Nature, vol. 414, Nov. 2001, pp. 105-111.
Schmeichel, et al., "Commentary: Modeling Tissue-Specific Signaling and Organ Function in Three Dimensions," Journal of Cell Science, 2003, 116 (12), pp. 2377-2388.
Schofield, et al., "Oxygen Sensing by HIF Hydroxylases," Nature Reviews, Molecular Cell Biology, vol. 5, May 2004, pp. 343-354.
Semenza, et al., "A Nuclear Factor Induced by Hypoxia via De Novo Protein Synthesis Binds to the Human Erythropoietin Gene Enhancer at a Site Required for Transcriptional Activation," Molecular and Cellular Biology, Dec. 1992, vol. 12, No. 12, pp. 5447-5454.
Shaw, et al., "Negative Photoresists for Optical Lithography," IBM Journal of Research and Development, vol. 41, No. 1/2, Jan./Mar. 1997, pp. 81-94, 15 pages.
Shimizu, et al., "Biofilm Formation on Hydrophilic Intraocular Lens Material," Current Eye Research, 31, 2006, pp. 989-997.
Sia, et al., "Microfluidic Devices Fabricated in Poly(dimethylsiloxane) for Biological Studies," Electrophoresis, 2003, 24, pp. 3563-3576.
Siegel, et al., "Foldable Printed Circuit Boards on Paper Substrates," Advanced Functional Materials, 2010, 20, pp. 28-35.
Smidsrod, et al., "Alginate as Immobilization Matrix for Cells," TibTech, Mar. 1990, vol. 8, pp. 71-78.
Smith, S.K., "Angiogenesis, Vascular Endothelial Growth Factor and the Endometrium," Hum. Reprod. Update 1998, 4, pp. 509-519.
Sodunke, et al., "Micropatterns of Matrigel for Three-Dimensional Epithelial Cultures," ScienceDirect, Biomaterials 28, 2007, pp. 4006-4016.
Su et al., "A Gene Atlas of the Mouse and Human Protein-Encoding Transcriptomes," PNAS, Apr. 2004, vol. 101, No. 16, pp. 6062-6067.
Tang, et al., "Molding of Three-Dimensional Microstructures of Geis," J. Am. Chem. Soc., 2003, 125, pp. 12988-12989.
Tonnesen, et al., "Review: Alginate in Drug Delivery Systems," Drug Development and Industrial Pharmacy, 28(6), 2002, pp. 621-630.
Urbich, et al., "Endothelial Progenitor Cells: Characterization and Role in Vascular Biology," Circulation Research, DOI: 10.1161/01.RES.0000137877.89448.78, Aug. 2004, pp. 343-353.

Vogel, et al., "Local Force and Geometry Sensing Regulate Cell Functions," Nature Reviews, Molecular Cell Biology, vol. 7, Apr. 2006, pp. 265-275.
von Lode, P., "Point-of-care Immunotesting: Approaching the Analytical Performance of Central Laboratory Methods," Clinical Biochemistry, 38, 2005, pp. 591-606.
Voytik-Harbin, et al., "Application and Evaluation of the Alamarblue Assay for Cell Growth and Survival of Fibroblasts," In Vitro Cell, 1998, pp. 239-246.
Wang, et al., "Anisotropic Hydrogel Thickness Gradient Films Derivatized to Yield Three-Dimensional Composite Materials," Langmuir, 2005, 21, pp. 8452-8459.
Washburn, E. W., "The Dynamics of Capillary Flow," The Physical Review, vol. XVII, No. 3, Second Series, Mar. 1921, pp. 273-283.
Weaver, et al., "Reversion of the Malignant Phenotype of Human Breast Cells in Three-Dimensional Culture and In Vivo by Integrin Blocking Antibodies," The Journal of Cell Biology, vol. 137, No. 1, Apr. 1997, pp. 231-245.
Winkleman, et al., "Fabrication and Manipulation of Ionotropic Hydrogels Cross-Linked by Paramagnetic Ions," Chem. Mater., 2007, 19, pp. 1362-1368.
Winkleman, et al., "Patterning micron-sized dfeatures in a cross-linked poly (acrylic acid) film by a wet etching process," The Royal Society of Chemistry, 2007, pp. 108-116.
Wong et al., "Directed Movement of Vascular Smooth Muscle Cells on Gradient-Compliant Hydrogels," Langmuir, 2003, 19, pp. 1908-1913.
Xerox Corporation, "Material Safety Data Sheet for Xerox Phaser 6250 Color Laser Toner," 2003, pp. E-1-E-5, retrieved from http://www.office.xerox.com/userdoc/P6250/6250_Web/pdfs/msds.pdf.
Xu, et al., "A Chemical Approach to Stem-Cell Biology and Regenerative Medicine," Nature, vol. 453, May 2008, pp. 338-344.
Yamada, et al., "Modeling Tissue Morphogenesis and Cancer in 3D," Cell 130, Aug. 2007, pp. 601-610.
Yeung, et al., "Effects of Substrate Stiffness on Cell Morphology, Cytoskeletal Structure, and Adhesion," Cell Motility and the Cytoskeleton, 60, 2005, pp. 24-34.
Yilmaz, et al., "Pten Dependence Distinguishes Haematopoietic Stem Cells from Leukaemia-Initiating Cells," Nature, vol. 441, May 2006, pp. 475-482.
Zguris, et al, "A Novel Single-Step Fabrication Technique to Create Heterogeneous Poly(ethylene glycol) Hydrogel Microstructures Containing Multiple Phenotypes of Mammalian Cells," Langmuir, 2005, 21, pp. 4168-4174.
Zhi, et al., "Multianalyte Immunoassay with Self-Assembled Addressable Microparticle Array on a Chip," Analytical Biochemistry, vol. 318, No. 2, Jul. 2003, pp. 236-243.
Zhu, et al., "Research Article: Proposal to Create Subspecies of Rickettsia Conorii Based on Multi-Locus Sequence Typing and an Emended Description of Rickettsia Conorii," BMC Microbiology, 2005, 5:11, 11 pages.
Zielhuis, et al., "Characterization of Holmium Loaded Alginate Microspheres for Multimodality Imaging and Therapeutic Applications," Journal of Biomedical Materials Research Part A, DOI 10.1002, 2007, pp. 892-898.

* cited by examiner

PAPER-BASED CELLULAR ARRAYS

CROSS-REFERENCE TO RELATED APPLICATIONS

This application claims the benefit of U.S. Provisional Application No. 61/040,030, filed Mar. 27, 2008; U.S. Provisional Application No. 61/040,010, filed Mar. 27, 2008; U.S. Provisional Application No. 61/097,718, filed Sep. 17, 2008; and U.S. Provisional Application No. 61/146,413, filed Jan. 22, 2009; the contents of all of which are hereby incorporated in their entirety herein.

GOVERNMENT SUPPORT

This invention was made with Government Support under Contract No. 5R01ES016665-02 awarded by the National Institutes of Health and grant HR011-04-1-0032 awarded by the Defense Advanced Research Projects Agency (DARPA). The Government has certain rights in the invention.

BACKGROUND

Cells in vivo reside in an organized three-dimensional environment as part of tissue and organ structures; loss of this tissue organization is a hallmark of cancer (Wodarz, et al., Nature Cell Biology 9:1016-1024 (2007); Lee, et al., J. Cell Sci. 121:1141-1150 (2008); Morrison, et al., Nature 441:1068-1074 (2006)). For nearly a century, progress in cancer research and discovery of anti-cancer agents have been fueled by investigations performed on cells cultured outside the living organism (ex vivo) (Ebeling, J. Exp. Med. 17:273-285 (1913); Carrel, et al., J. Exp. Med. 13:387-U34 (1911); Carrel, et al., J. Exp. Med. 13:571-575 (1911); Leighton, Cancer Res. 17:929-941 (1957); Paul, Cancer Res. 22:431-& (1962)). The majority of these studies have been performed with cells cultured on two dimensional surfaces. Morphological and functional differences of cells cultured in these conditions and cells in vivo have been widely recognized, and three-dimensional cell growth substrates have been shown to present a more physiologically relevant model of in vivo cell environment (Yamada, et al., Cell 130:601-610 (2007); Nelson, et al., Annu. Rev. Cell Dev. Biol. 22:287-309 (2006); Huang, et al., Nature cell biology 1:E131-E138 (1999); Schmeichel, et al., J. Cell Sci. 116, 2377-2388 (2003)). Importantly, cells cultured on two-dimensional substrates often do not respond to soluble factors that influence cells in three-dimensional environments (Emerman, et al., In Vitro-Journal of the Tissue Culture Association 13:316-328 (1977); Emerman, et al., Proc. Natl. Acad. Sci. U.S.A. 74:4466-4470 (1977); Cukierman, et al., Science 294:1708-1712 (2001); Bissell, et al., Differentiation 70:537-546 (2002); Weaver, et al., J. Cell Biol. 137:231-245 (1997)). Yet, to date, the majority of drug discovery processes start from small-molecule screening in two-dimensional culture-based assays. Failures of the identified compounds in animal and human trials drive the cost of drug discovery to >$1 billion per new compound (Griffith, et al., Nat. Rev. Mol. Cell Biol. 7:211-224 (2006)). High-throughput assays based on three-dimensional cultures can allow assessment of drug efficacy and toxicity at the very first step of the drug discovery process. Integration of the three-dimensional cell culture into every aspect of basic and applied cancer research will advance the discovery of new therapeutics for cancer treatment.

Differences in cell responses in three-dimensional vs. two-dimensional environment originate from differences in cell polarity, cellwide distribution of the substrate adhesion sites and responses of cells to mechanical properties of the matrix (Yamada, et al. 2007; Huang, et al., 1999). On the molecular level, these events are regulated by the cross-talk between integrin signaling pathways and those of the receptor-tyrosine kinases. Properties like chemical composition of the matrix, nano- and microscale distribution of the integrin ligands (Cukierman, et al., 2001; Chen, et al., Science 276:1425-1428 (1997)), as well as mechanical property of the matrix (Engler, et al., Cell 126:677-689 (2006); Pelham, et al., Proc. Natl. Acad. Sci. U.S.A. 94:13661-13665 (1997); Yeung, et al., Cell Motil. Cytoskeleton 60:24-34 (2005)), can influence these pathways and modulate cell behavior. Furthermore, delivery of oxygen and nutrients to cells in gel-like matrix is driven by diffusion; hence, physical dimensions of the matrix also play a role in three-dimensional cell culture. Due to diffusion limitations, proliferation of cells in three-dimensional matrices ex vivo is often limited to a depth of less than a few hundred microns. Therefore, the size, composition, and mechanical properties of the matrix must be carefully controlled in three-dimensional culture.

After decades of side-by-side development of two-dimensional and three-dimensional culture, the simplicity of two-dimensional culture approach makes it a dominant technology for ex vivo investigation of cells. The need to control multiple chemical and physical properties of the matrix makes three-dimensional culture of cells more labor intensive and less reproducible.

SUMMARY

In one aspect, the invention features a three-dimensional cellular array. The cellular array includes a porous, hydrophilic substrate comprising a plurality of porous regions, each porous region bounded at least in part by a liquid impervious boundary; and a hydrogel comprising cells, wherein the hydrogel is embedded within the porous regions. In one embodiment, the substrate is paper, nitrocellulose, cellulose acetate, cloth, or porous polymer film.

In one embodiment, the hydrogel is a temperature sensitive hydrogel. In particular embodiments, the temperature-sensitive hydrogel is MATRIGEL™ or collagen. In some embodiments, the hydrogel is an ionotropic hydrogel. In particular embodiments, the ionotropic hydrogel comprises alginic acid (AA), carboxymethylcellulose (CMC), ι-carrageenan, poly(galacturonic acid) (PG), poly(bis(4-carboxyphenoxy)-phosphazene, or PuraMatrix.

In yet other embodiments, the liquid impervious boundary comprises PDMS, poly(lactic-co-glycolic acid), epoxy, polystyrene, a polyether, a polyamide, PMMA, polycarbonate, polyethylene, polypropylene, a photoresist precursors, a wax or a fat.

In certain embodiments, the array comprises 1, 2, 3, 4, 5, 10, 25, 50, 100, 150, 200, 250, 300, 400, 500, 1,000 or more porous regions, each bound by a liquid impervious boundary. In particular embodiments, the array comprises 96, 384, 1536, or 3456 porous regions, each bound by a liquid impervious boundary.

In some embodiments, the cells are bacterial cells, insect cells, yeast cells, or mammalian cells.

In another aspect, the invention features a method of making a three-dimensional cellular array. The method comprises providing a porous, hydrophilic substrate, wherein the substrate comprises a plurality of porous regions, each porous region bounded at least in part by a liquid impervious boundary; and contacting the porous, hydrophilic substrate with a suspension of cells and a temperature-sensitive hydrogel or an ionotropic hydrogel precursor, wherein the suspension saturates one or more porous regions of the substrate. In one embodiment, the substrate is paper, nitrocellulose, cellulose acetate, cloth, or porous polymer film.

In one embodiment, the hydrogel is a temperature sensitive hydrogel. In particular embodiments, the temperature-sensitive hydrogel is MATRIGEL™ or collagen. In some embodiments, the hydrogel is an ionotropic hydrogel. In particular embodiments, the ionotropic hydrogel comprises alginic acid (AA), carboxymethylcellulose (CMC), ι-carrageenan, poly(galacturonic acid) (PG), poly(bis(4-carboxyphenoxy)-phosphazene, or PuraMatrix.

In one embodiment, the method further comprising wetting, e.g., saturating, the substrate with a gelling agent before contacting the suspension of cells with the substrate. In some embodiments, the gelling agent is a metallic ion. In particular embodiments, the gelling agent is $Pb^{2+}$, $Ba^{2+}$, $Fe^{3+}$, $Al^{3+}$, $Cu^{2+}$, $Cd^{2+}$, $Ho^{3+}$, $Ca^{2+}$, $Zn^{2+}$, $Co^{2+}$, $Ni^{2+}$, $Mn^{2+}$, or $Mg^2$.

In some embodiments, the liquid impervious boundary comprises PDMS, poly(lactic-co-glycolic acid), epoxy, polystyrene, a polyether, a polyamide, PMMA, polycarbonate, polyethylene, polypropylene, a photoresist precursors, a wax or a fat.

In certain embodiments, the array comprises 1, 2, 3, 4, 5, 10, 25, 50, 100, 150, 200, 250, 300, 400, 500, 1,000 or more porous regions, each bound by a liquid impervious boundary. In particular embodiments, the array comprises 96, 384, 1536, or 3456 porous regions, each bound by a liquid impervious boundary.

In some embodiments, the cells are bacterial cells, insect cells, yeast cells, or mammalian cells.

In another aspect, the invention features a method of making a three-dimensional cellular array. The method comprises providing a porous, hydrophilic substrate; contacting a plurality of defined regions of the substrate with a suspension, the suspension comprising cells and a temperature-sensitive hydrogel or an ionotropic hydrogel precursor, wherein the suspension saturates the plurality of defined regions of the substrate; and contacting the temperature-sensitive hydrogel or the ionotropic hydrogel precursor with a gelling agent, wherein the gelling agent induces the formation of a hydrogel embedded in the plurality of defined regions of the substrate. In one embodiment, the substrate is paper, nitrocellulose, cellulose acetate, cloth, or porous polymer film.

In one embodiment, the hydrogel is a temperature sensitive hydrogel. In particular embodiments, the temperature-sensitive hydrogel is MATRIGEL™ or collagen. In some embodiments, the hydrogel is an ionotropic hydrogel. In particular embodiments, the ionotropic hydrogel comprises alginic acid (AA), carboxymethylcellulose (CMC), ι-carrageenan, poly(galacturonic acid) (PG), poly(bis(4-carboxyphenoxy)-phosphazene, or PuraMatrix.

In one embodiment, the method further comprising wetting, e.g., saturating, the substrate with a gelling agent before contacting the suspension of cells with the substrate. In some embodiments, the gelling agent is a metallic ion. In particular embodiments, the gelling agent is $Pb^{2+}$, $Ba^{2+}$, $Fe^{3+}$, $Al^{3+}$, $Cu^{2+}$, $Cd^{2+}$, $Ho^{3+}$, $Ca^{2+}$, $Zn^{2+}$, $Co^{2+}$, $Ni^{2+}$, $Mn^{2+}$, or $Mg^2$.

In some embodiments, the cells are bacterial cells, insect cells, yeast cells, or mammalian cells. In some embodiments, the method further comprising contacting the array with a culture medium.

In another aspect, the invention features a method of identifying an agent that modifies cellular function. The method comprises providing an array described herein; contacting the array with one or more test agents; and detecting one or more cellular functions in the presence of the one or more test agents; wherein a change in cellular function in the presence of the one or more test agents indicates the one or more test agents modify cellular function.

In some embodiments, the array includes a porous, hydrophilic substrate comprising a plurality of porous regions, each porous region bounded at least in part by a liquid impervious boundary; and a hydrogel comprising cells, wherein the hydrogel is embedded within the porous regions. In one embodiment, the substrate is paper, nitrocellulose, cellulose acetate, cloth, or porous polymer film.

In one embodiment, the hydrogel is a temperature sensitive hydrogel. In particular embodiments, the temperature-sensitive hydrogel is MATRIGEL™ or collagen. In some embodiments, the hydrogel is an ionotropic hydrogel. In particular embodiments, the ionotropic hydrogel comprises alginic acid (AA), carboxymethylcellulose (CMC), ι-carrageenan, poly(galacturonic acid) (PG), poly(bis(4-carboxyphenoxy)-phosphazene, or PuraMatrix.

In yet other embodiments, the liquid impervious boundary comprises PDMS, poly(lactic-co-glycolic acid), epoxy, polystyrene, a polyether, a polyamide, PMMA, polycarbonate, polyethylene, polypropylene, a photoresist precursors, a wax or a fat.

In certain embodiments, the array comprises 1, 2, 3, 4, 5, 10, 25, 50, 100, 150, 200, 250, 300, 400, 500, 1,000 or more porous regions, each bound by a liquid impervious boundary. In particular embodiments, the array comprises 96, 384, 1536, or 3456 porous regions, each bound by a liquid impervious boundary.

In some embodiments, the array is contacted with the one or more test agents at a plurality of porous regions. In particular embodiments, the array is contacted with the one or more test agents at 96, 384, 1536, or 3456 porous regions. In some embodiments, each porous region is contacted with a different test agent.

In some embodiments, the test agent is a small organic or inorganic molecule, an amino acid, a polypeptide, a nucleic acid, a peptide nucleic acid, a carbohydrate, or a polysaccharide. In some embodiments, the test agent is a member of a library of test agents, e.g., a combinatorial chemical library.

In other embodiments, the cellular function is proliferation, migration, viability, or gene transcription.

In another aspect, the invention features a method of identifying an agent that modifies cellular function. The method comprises providing a three-dimensional array described herein; cutting the substrate into a plurality of segments, each segment having equal dimensions; contacting each segment with a test agent or a control; and detecting one or more cellular functions in the presence of the test agent; wherein a change in cellular function in the presence of the test agent indicates the test agent modifies cellular function. In some embodiments, the cellular function is proliferation, migration, viability, or gene transcription.

In some embodiments, each segment is placed in a well of a 96-well, 384-well, 1536-well, or 3456-well plate. In some embodiments, each well contains a different test agent. In some embodiments, the test agent is a small organic or inorganic molecule, an amino acid, a polypeptide, a nucleic acid, a peptide nucleic acid, a carbohydrate, or a polysaccharide. In some embodiments, the test agent is a member of a library of test agents, e.g., a combinatorial chemical library.

In some embodiments, the cells are bacterial cells, insect cells, yeast cells, or mammalian cells.

In another aspect, the invention features a three-dimensional microarray. The microarray comprises a bottomless microtiter plate having a plurality of wells; and a porous hydrophilic substrate comprising a plurality of porous regions and a plurality of liquid impervious boundaries, each porous region bounded by a liquid impervious boundary; wherein the wells and the liquid impervious boundaries are arranged in identical patterns, the microtiter plate and the substrate attached so that the plurality of wells are aligned and sealingly joined to the plurality of liquid impervious boundaries to form an individual chamber for each porous region. In some embodiments, the porous regions of the substrate comprise cells in a hydrogel.

In one embodiment, the hydrogel is a temperature sensitive hydrogel. In particular embodiments, the temperature-sensitive hydrogel is MATRIGEL™ or collagen. In some embodiments, the hydrogel is an ionotropic hydrogel. In particular embodiments, the ionotropic hydrogel comprises alginic acid (AA), carboxymethylcellulose (CMC), ι-carrageenan, poly(galacturonic acid) (PG), poly(bis(4-carboxyphenoxy)-phosphazene, or PuraMatrix.

In yet other embodiments, the liquid impervious boundary comprises PDMS, poly(lactic-co-glycolic acid), epoxy, polystyrene, a polyether, a polyamide, PMMA, polycarbonate, polyethylene, polypropylene, a photoresist precursors, a wax or a fat.

In certain embodiments, the array comprises 1, 2, 3, 4, 5, 10, 25, 50, 100, 150, 200, 250, 300, 400, 500, 1,000 or more porous regions, each bound by a liquid impervious boundary. In particular embodiments, the array comprises 96, 384, 1536, or 3456 porous regions, each bound by a liquid impervious boundary.

In some embodiments, the cells are bacterial cells, insect cells, yeast cells, or mammalian cells.

In another aspect, the invention features a method of identifying an agent that modifies cellular function. The method comprises providing a microarray comprising a bottomless microtiter plate having a plurality of wells; and a porous flexible substrate comprising a plurality of porous regions and a plurality of liquid impervious boundaries, each porous region bounded by a liquid impervious boundary; wherein the wells and the liquid impervious boundaries are arranged in identical patterns, the microtiter plate and the substrate attached so that the plurality of wells are aligned and sealingly joined to the plurality of liquid impervious boundaries to form an individual chamber for each porous region; contacting the array with one or more test agents; and detecting one or more cellular functions in the presence of the one or more test agents; wherein a change in cellular function in the presence of the one or more test agents indicates the one or more test agents modify cellular function.

In some embodiments, the test agent is a small organic or inorganic molecule, an amino acid, a polypeptide, a nucleic acid, a peptide nucleic acid, a carbohydrate, or a polysaccharide. In some embodiments, the test agent is a member of a library of test agents, e.g., a combinatorial chemical library. In some embodiments, each well contains a different test agent.

In another aspect, the invention features a method of patterning a porous, hydrophobic substrate. The method comprises contacting a porous, hydrophobic substrate with an aqueous solution comprising a water-soluble compound, the solution infiltrating the substrate to form a first region of the substrate that is saturated with the solution and a second region that is not contacted with the solution; contacting the substrate with a hydrophobic material, the hydrophobic material saturating the second region; and removing the water-soluble compound, resulting in a hydrophilic porous region that is bounded by the hydrophobic material.

In some embodiments, the water-soluble compound is sucrose, trehalose, glucose, fructose, xylitol, ribose, threitol, mannose, or glycerol. In some embodiments, the aqueous solution is spotted, printed, drawn, or stamped onto the porous, hydrophobic substrate. In particular embodiments, the solution is printed using an inkjet printer.

In some other embodiments, the hydrophobic material comprises PDMS, poly(lactic-co-glycolic acid), epoxy, polystyrene, a polyether, a polyamide, PMMA, polycarbonate, polyethylene, polypropylene, a photoresist precursors, a wax or a fat.

In certain embodiments, the substrate is patterned into 1, 2, 3, 4, 5, 10, 25, 50, 100, 150, 200, 250, 300, 400, 500, 1,000 or more porous regions, each bound by the hydrophobic material. In particular embodiments, the substrate is patterned into 96, 384, 1536, or 3456 porous regions, each bound by a liquid impervious boundary.

In some embodiments, the substrate is nitrocellulose, cellulose acetate, cellulosic paper, filter paper, cloth, or a porous polymer film.

In another aspect, the invention features a method of patterning a porous, hydrophobic substrate. The method comprises contacting a porous, hydrophobic substrate with a hydrophobic material, the hydrophobic material saturating the substrate; contacting a region of the substrate with an aqueous solution comprising a water-soluble compound, the solution displacing the hydrophobic material from the region; and removing the water-soluble compound, resulting in a hydrophilic porous region that is bounded by the hydrophobic material.

In some embodiments, the water-soluble compound is sucrose, trehalose, glucose, fructose, xylitol, ribose, threitol, mannose, or glycerol. In some embodiments, the aqueous solution is spotted, printed, drawn, or stamped onto the porous, hydrophobic substrate. In particular embodiments, the solution is printed using an inkjet printer.

In some other embodiments, the hydrophobic material comprises PDMS, poly(lactic-co-glycolic acid), epoxy, polystyrene, a polyether, a polyamide, PMMA, polycarbonate, polyethylene, polypropylene, a photoresist precursors, a wax or a fat.

In certain embodiments, the substrate is patterned into 1, 2, 3, 4, 5, 10, 25, 50, 100, 150, 200, 250, 300, 400, 500, 1,000 or more porous regions, each bound by the hydrophobic material. In particular embodiments, the substrate is patterned into 96, 384, 1536, or 3456 porous regions, each bound by a liquid impervious boundary.

In some embodiments, the substrate is nitrocellulose, cellulose acetate, cellulosic paper, filter paper, cloth, or a porous polymer film.

In some aspects, an array described herein can include cells embedded within a porous, hydrophilic substrate in the absence of a hydrogel.

BRIEF DESCRIPTION OF THE DRAWINGS

The foregoing and other objects of the present invention, the various features thereof, as well as the invention itself, may be more fully understood from the following description, when read together with the accompanying drawings, in which.

DETAILED DESCRIPTION

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

General

The invention is based, at least in part, on the production and use of three-dimensional paper-based cellular arrays. The use of micro-fabricated substrates for the generation of three-dimensional cell cultures of uniform characteristic is difficult to adopt universally, as many cell biology research groups lack the expertise or the equipment used for micro-fabrication (e.g., a clean room). In addition, many micro-fabrication techniques are well-suited for investigating small numbers of cells, but they are difficult to adopt for large scale assays and screens. Breakthroughs in three-dimensional cell-based assays hinge on simple and scalable techniques that allow for control of all desired properties of the three-dimensional matrix. The methods described herein can be used to produce such three-dimensional matrices.

Three-Dimensional Cellular Arrays

Figures 1A, 1B:
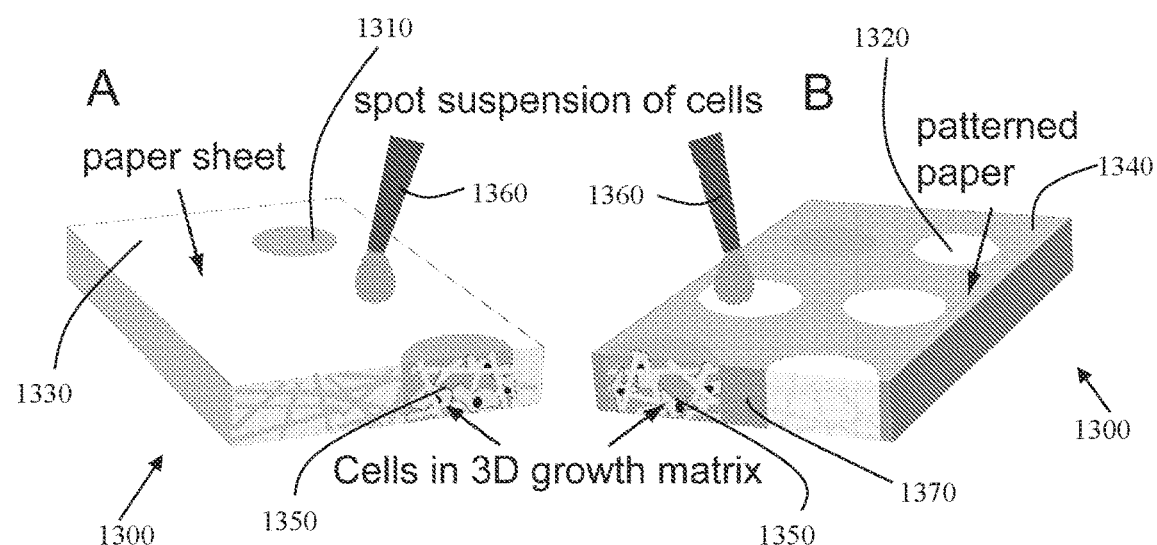
FIG. 1A is a schematic illustrating the fabrication of three-dimensional cellular arrays using plain paper.
FIG. 1B is a schematic illustrating the fabrication using paper patterned into hydrophilic and hydrophobic regions.

In certain instances, the present disclosure provides three-dimensional cellular arrays capable of growing and maintaining cells. The cellular arrays include a porous flexible substrate and a cell-containing hydrogel embedded within the substrate. Exemplary three-dimensional cellular arrays are illustrated schematically in FIGS. 1A and 1B 1A As depicted in FIGS. 1A and 1B, a three-dimensional cellular array 1300 includes areas, or "wells", 1310, 1320 within the substrate 1330, 1340. The wells contain cells within a three-dimensional hydrogel 1350 that is infused within the porous network of the substrate. The substrate provides a 3D scaffolding in which the cells can reside.

As described herein, the cellular array can be made by contacting, e.g., spotting, the substrate with a suspension of cells in a hydrogel or hydrogel precursor, as illustrated in FIGS. 1A and 1B, using an applicator 1360. As the substrate is porous and hydrophilic, the dimensions of the wells 1310 are dictated by the thickness of the substrate as well as the distance the suspension of cells wicks or spreads laterally through the substrate 1330 (see FIG. 1A). Because liquids and gels yield spots of defined lateral dimensions when spotted onto paper or other porous hydrophilic substrates, three-dimensional cell cultures of desired lateral dimensions can be obtained by spotting defined volumes of a suspension of cells in a hydrogel precursor onto the porous hydrophilic substrate. The lateral dimensions of the spot (i.e., the lateral size of the three dimensional culture) can be controlled by controlling the volume of the spotted liquid. Vertical dimensions (thickness) of the three dimensional culture are defined by the thickness of the hydrophilic material. Repetition of the spotting process yields patterned three-dimensional cultures on a single piece of paper (i.e., arrays of cells). The spotting can be performed such that the resulting patterns can be readily recognized by an existing cell culture and screening interface (e.g., 384-well layout can be generated by spotting a 16×24 array of spots with 4.5 mm vertical and horizontal pitch).

When the substrate is patterned, e.g., contains hydrophilic and hydrophobic areas, as is illustrated by substrate 1340 in FIG. 1B the dimensions of the wells 1320 are dictated by the thickness of the substrate and the size of the hydrophilic areas of the substrate (see FIG. 1B). In such embodiments, the hydrophilic regions are bounded by hydrophobic barriers or walls 1370, which limit the lateral flow of the suspension of cells.

After contacting the substrate with a suspension of cells and a hydrogel or hydrogel precursor, the substrate is maintained under suitable conditions that allow gelation of the hydrogel within the substrate. As described herein, suitable conditions include maintaining the substrate at a particular temperature or contacting the substrate with a gelling agent. The resulting three-dimensional cellular array is stable and can be maintained in conditions suitable for cell growth. Such culture conditions are known in the art (see, e.g., Culture of Animal Cells: A Manual of Basic Techniques, Freshney, R. I. ed., (Alan R. Liss & Co., New York 1987); Animal Cell Culture: A Practical Approach, Freshney, R. I. ed., (IRL Press, Oxford, England 1986)). For example, the cellular array can be immersed in cell culture medium suitable for a particular cell type and maintained in an incubator.

Figures 1C, 1D:
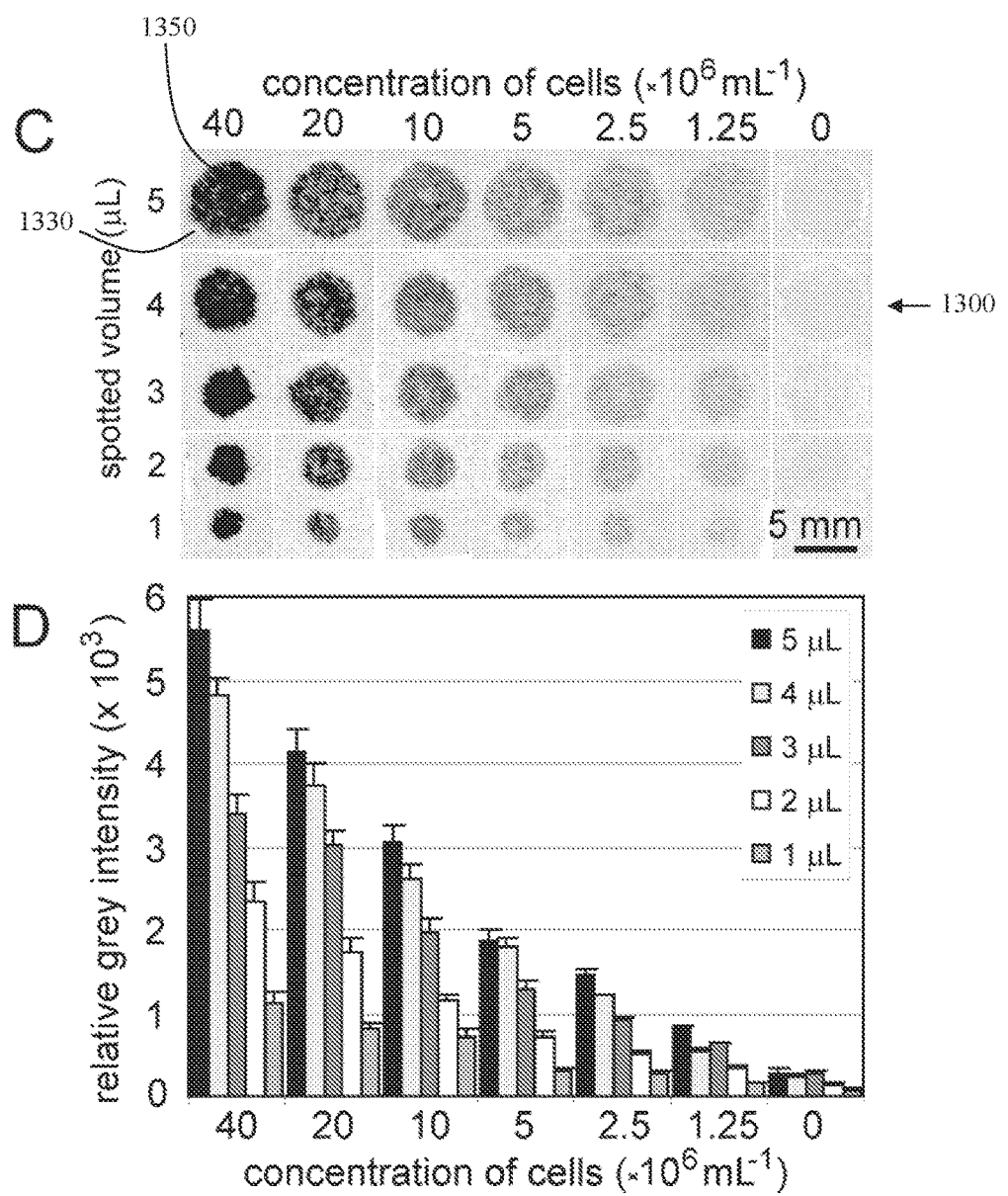
FIG. 1C is a stitched mosaic of representative scanned images of chromatography paper spotted with suspensions of HS-5 stromal cells in MATRIGEL™ and stained with Alexa Fluor 633-conjugated phalloidine.
FIG. 1D is a graph of the average from 4-6 measurements from FIG. 1C, and the error bar is equal to one standard deviation.

FIG. 1C is a series of images depicting three-dimensional cellular arrays 1300 of FIG. 1A. In the exemplary arrays depicted in FIG. 1C, 1-5 µL of HS-5 cells suspended in MATRIGEL™ were spotted onto chromatography paper 1330 with a hand-held Gilson P10 pipette. Suspensions of different concentrations of cells were used to vary the number of cells per spotted area. The spotted paper was immersed in 37° C. culture medium for 24 hours. The paper was then fixed with formaldehyde, stained with Alexa Fluor 633-conjugated phalloidin and imaged using Typhoon gel scanner. The displayed image is a stitched mosaic of representative scanned images of each spotted area. Image quantification was performed using ImageJ.

Controlling the spotted volume allowed the regulation of the lateral dimension of the cell-filled areas. As shown in FIG. 1C, cell-filled areas 1350 having diameters of 2-8 mm were produced by spotting 1-5 µL of a MATRIGEL™ suspension. The concentration of cells in the spotted solution was varied, while keeping lateral dimensions of the cell growth area constant. The cell density in paper was evaluated by measuring the grey scale intensity of the cell-containing areas in the scanned images (depicted in FIG. 1D). As FIG. 1C demonstrates, spotting of suspensions of cells in MATRIGEL™ allows for reproducible generation of three-dimensional matrices of defined thickness and lateral dimensions that present well-defined numbers of cells. Furthermore, cell density in paper-supported matrices can be rapidly quantified using a conventional gel scanner.

Figures 1E, 1F:
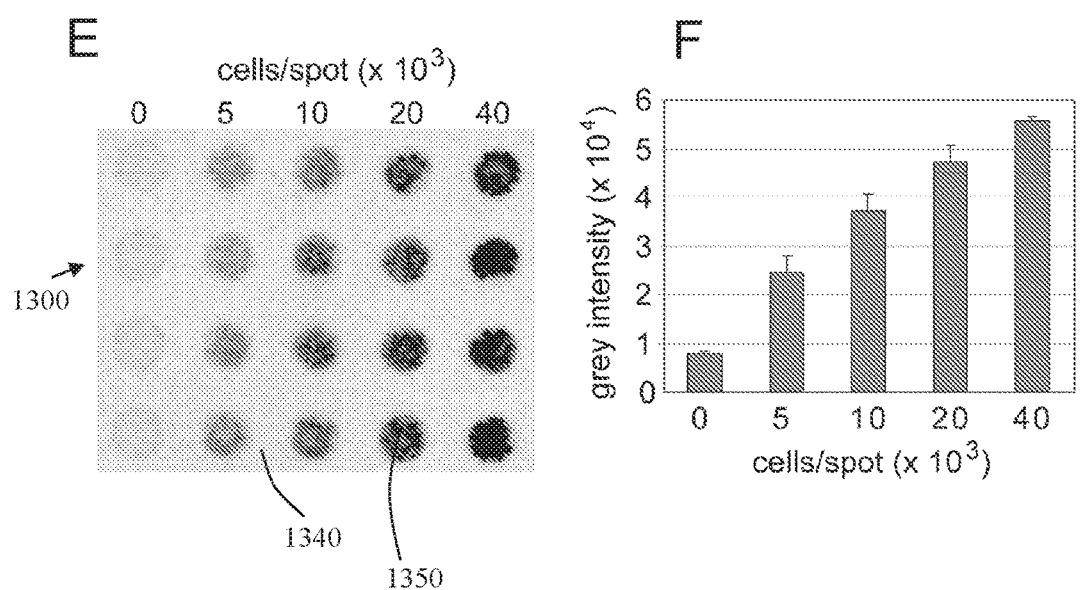
FIG. 1E is a gel scanner image of suspensions of HUVEC cells in MATRIGEL™ spotted onto SU8-patterned paper, suspended in culture media for 24 hours, fixed, and stained with SYTOX dye.
FIG. 1F is a graph of the average from 4-6 measurements from FIG. 1E.

FIG. 1E is an image depicting a three-dimensional cellular array 1300 of FIG. 1B on a patterned substrate 1340. In the exemplary array depicted in FIG. 1E, cells embedded in the wells of the cellular array were visualized using standard fluorescent and colorimetric techniques. A fluorescent gel scanner was used for quantitative characterization. The number of cells in areas 1350 of patterned substrate 1340 was determined when cells were stained with SYTOX dye (see FIG. 1F).

The cellular arrays described herein can be fabricated from porous, hydrophilic substrates. In some embodiments, the substrate is paper, such as chromatographic paper. However, any substrate that wicks fluids by capillary action can be used, including, but not limited to, nitrocellulose and cellulose acetate, cellulosic paper, filter paper, cloth, and porous polymer film.

Many physical parameters of paper make it an attractive candidate for supporting the three-dimensional culture of cells: (1) Paper is an inexpensive, non-toxic, inert porous matrix; (2) flat paper sheets of well-defined thickness (>20 µm) are readily available world-wide; (3) paper can be patterned into hydrophilic and hydrophobic areas; aqueous solutions readily adopt the dimensions of the hydrophilic areas; (4) mechanical properties of the paper can be varied; and (5) paper can be easily shaped, layered or folded into different forms. Based on these properties, paper can serve as the mold for natural or synthetic cell-adhesive hydrogels. Paper can be used as received, or without introduction of hydrophobic walls to define the wells. Upon wicking into the paper, the size and the thickness of the hydrogel is dictated by that of the paper (see, e.g., FIG. 1A).

In some instances, the three-dimensional cellular arrays are made using patterned substrates, e.g., patterned paper. Because liquids and gels can readily wick into paper substrates, patterning the paper with liquid impermeable (hydrophobic) borders can be used to dictate not only the physical dimensions but also the shape of the cell growth substrate. Accordingly, in some embodiments, the substrate is patterned into hydrophobic and hydrophilic regions. Any method of patterning the hydrophilic substrate can be used. By way of example, the hydrophobic layer can be applied directly to the porous substrate to produce patterned regions having hydrophilic or hydrophobic properties using printing, such as from an ink jet printer, liquid transfer, such as in stamping or other printing methods, or silk screening. The hydrophobic pattern can also be made using photolithography, in which the paper is infused with photoresist and then exposed to light to produce regions of hydrophobic photoresist and regions of hydrophilic resist-free paper. Exemplary methods are known in the art and described in, e.g., WO 2008/049083, which is incorporated in its entirety by reference.

Exemplary methods for fabricating these patterned paper substrates include a photo-patterning technique, in which a paper is soaked with commercially available photo-reactive polymer (e.g., SU8), and a transparency that presents the desired pattern is overlaid and the paper is briefly exposed to UV light. Upon washing with a suitable solvent, e.g., acetone, the polymer is removed from the exposed areas yielding desired pattern.

Another exemplary method is described herein as "Sweet Patterning". In certain embodiments, a substrate described herein is patterned using water-soluble compounds, such as sugars or their derivatives (e.g., polyols, e.g., xylitol). These methods stem from the observation that hydrophobic solutions cannot penetrate into regions of paper infused with aqueous solutions. Instead, hydrophobic solvents form complementary patterns within the paper (see, e.g., FIG. 2A). Accordingly, a portion of the hydrophilic substrate can be contacted with a water-soluble compound, which infiltrates the porous substrate to form a region of a specific shape that is saturated with an aqueous solution containing the water-soluble compound. Solvents other than water that can solubilize polar compounds and that are immiscible with the corresponding hydrophobic solvent can also be used. The substrate can then be contacted with a hydrophobic material, which saturates the exposed area of the substrate, but does not penetrate into the water saturated regions. The hydrophobic material can contain a polymer or polymer precursor, which can be treated to set or cure the polymer, for example by heat, evaporation or photopolymerization. The water-soluble compound can subsequently be removed from the hydrophilic substrate, leaving a hydrophilic porous region that is defined by the hydrophobic material. In certain embodiments, the water-soluble compound is sucrose, e.g., in an aqueous solution. In other embodiments, the hydrophobic material is, e.g., PDMS, polystyrene, or any other hydrophobic material that is soluble in the solvent used to generate the hydrophobic solution.

In some embodiments, the substrate is contacted with the water-soluble compound by, e.g., spotting, printing, drawing, or stamping. In a patterning strategy based on conventional inkjet printing, the inverse of a desired hydrophobic pattern is created by printing sucrose solution onto the paper. The paper is then immersed into a solution of polystyrene (or other polymer) that fills the sucrose-free regions. Upon washing with water, the sucrose template is removed and desired hydrophilic-hydrophobic pattern is obtained.

Figure 2A:
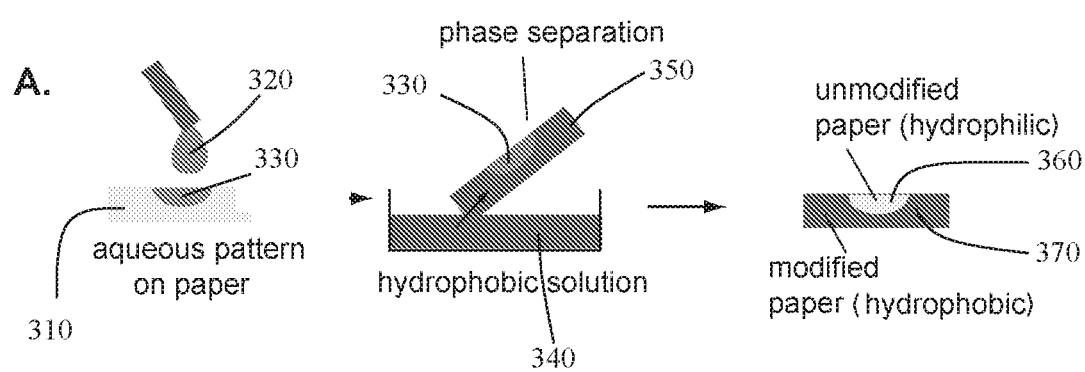
FIG. 2A is a schematic of a process for patterning hydrophobic materials onto paper by pretreating the paper with an aqueous solution of carbohydrates ("sweet patterning").

FIG. 2A schematically illustrates one method for patterning a hydrophilic, porous substrate 310, e.g., paper, with an aqueous solution 320, e.g., an aqueous solution of a water-soluble compound, e.g., an aqueous solution of sucrose. In this example, an aqueous solution of sucrose is spotted onto paper, which forms a water solution saturated region 330 in the paper. The paper is then immersed within a hydrophobic solution 340. The hydrophobic solution can be a solution of any polymer in a hydrophobic solvent that is immiscible with the aqueous solution. For example, the hydrophobic solution can contain polymer precursors (e.g., PDMS) or polymers (e.g., polystyrene, PLGA). The two immiscible liquids phase separate on the porous substrate to provide aqueous region 330 and hydrophobic region 350. Due to phase separation, the hydrophobic solution does not modify the area of the paper onto which the aqueous solution was spotted. The hydrophobic solution can be treated to set or cure the polymer, for example, by heating, evaporation or photocuring. The sucrose can then be washed away, e.g., with water, resulting in a paper patterned with the hydrophobic material. The resultant substrate includes areas of hydrophilic unmodified paper 360 and hydrophobic modified paper 370. Immiscible liquids within porous substrate can template each other: hydrophobic solvents form complementary shapes around hydrophilic patterns on the substrate.

Although the schematic in FIG. 2A illustrates pretreating the substrate with the water-soluble compound and subsequently treating the substrate with the hydrophobic material, in other embodiments, the substrate can be pretreated with the hydrophobic material and subsequently treated with the water-soluble compound (see, e.g., FIG. 4). This is illustrated in FIG. 4, in which a substrate is completely soaked in a hydrophobic solution to produce hydrophobic base 510. The hydrophobic solution includes a polymer as described above. In this example, a water solution 520 is spotted onto paper, which forms a water solution saturated region 530 in the paper. The water solution is immiscible in the hydrophobic solution and forms an aqueous region 530 in the hydrophobic base 510. The substrate may be treated as described above to provide substrate includes areas of hydrophilic unmodified paper and hydrophobic modified paper (not shown).

Any of a number of known techniques can be used to apply the water-soluble compound to the substrate to produce hydrophilic templates. For example, an aqueous solution of a water-soluble compound can be applied by spotting, printing, drawing, or stamping (see, e.g., FIG. 5 and Example 11). Printing techniques are known and include the use of inkjet printers, fountain pens, and the like. The aqueous solution can also be applied by drawing, such as silk screening, doctor blading, and the like. For stamping techniques, stamps can be made of known materials, e.g., rubber, metal and paper, designed to hold and transfer the desired amount of liquid (see, e.g., FIG. 5D). Other known methods for applying liquids, inks, solvents, dyes, and the like to a substrate can also be used in the methods described herein. The application can be by hand or using a machine, e.g., an automated system.

The methods described herein can utilize any water-soluble compound. These can include, e.g., sucrose, trehalose, glucose, fructose, xylitol, ribose, threitol, mannose, glycerol and other water soluble carbohydrates and their derivatives at least as soluble as those listed above. The appropriate concentration of a water-soluble compound to use on a given substrate and with a given hydrophobic material can be determined using, e.g., the assay described in Example 1 herein. In some embodiments, the water-soluble compound can be insoluble in non-polar organic solvents. In some embodiments, the water-soluble compound is an inorganic salt.

The patterning techniques based on general phase separation described herein can be used to pattern many types of hydrophobic materials onto the paper. For example, the hydrophobic material can be PDMS, poly(lactic-co-glycolic acid), epoxy or polystyrene. Other hydrophobic materials that can be used include, without limitation, any plastic that can be soluble in organic solvents (e.g., polystyrene and derivatives, polyethers, polyamides, PMMA, polycarbonate, polyethylene, polypropylene, photoresist precursors (e.g., SU8), waxes and fats), and/or that can be made by, e.g., polymerization of polycondensation from organic solvents at, e.g., 20-70° C. (e.g., PDMS, polyurethane and epoxy derivatives, phenol-formaldehyde polymers or acrylate and matecrylate derivatives).

Hydrogels

A cellular array described herein can be produced by contacting a substrate with a hydrogel or hydrogel precursor, which wicks into the hydrophilic substrate. In certain embodiments, a hydrogel is formed after a precursor has been applied to the substrate. The hydrogel is used with both patterned and unpatterned porous substrates as described herein.

Any known hydrogel can be used in the methods described herein. Hydrogel matrices are described, for example, in U.S. Pat. No. 5,906,934; Lin et al., Advanced Drug Delivery Rev. 58: 1379-1408 (2006); and Jen et al., Biotechnology and Bioengineering 50: 357-364 (2000). Polymers that can form ionic or covalently crosslinked hydrogels that are malleable can be used in the methods described herein. A "hydrogel", as used herein, is a substance formed when a polymer is cross-linked via covalent, ionic, or hydrogen bonds to create a three-dimensional open-lattice structure that entraps water molecules to form a gel. The polymer can be an organic polymer. The polymer can be a natural or synthetic polymer. As used herein, a "hydrogel precursor" is a polymer that can be cross-linked via covalent, ionic, or hydrogen bonds to form a hydrogel.

Examples of materials that can be used to form a hydrogel include polysaccharides such as alginate, polyphosphazines, and polyacrylates (which are crosslinked ionically) or block copolymers such as Pluronics™ or Tetronics™, polyethylene oxide-polypropylene glycol block copolymers (which are crosslinked by temperature or pH, respectively). Other materials include proteins such as fibrin, polymers such as polyvinylpyrrolidone, hyaluronic acid, and collagen. In general, these polymers are at least partially soluble in aqueous solutions, such as water, buffered salt solutions, or aqueous alcohol solutions, that have charged side groups, or a monovalent ionic salt thereof.

Nonlimiting examples of polymers with acidic side groups that can be reacted with cations include poly(phosphazenes), poly(acrylic acids), poly(methacrylic acids), copolymers of acrylic acid and methacrylic acid, poly(vinyl acetate), sulfonated polymers, such as sulfonated polystyrene. Other nonlimiting examples include, e.g., alginic acid (AA), carboxymethylcellulose (CMC), L-carrageenan, poly (galacturonic acid) (PG), poly(acrylic acid) (PAA), and poly(bis(4-carboxyphenoxy)-phosphazene. Copolymers having acidic side groups formed by reaction of acrylic or methacrylic acid and vinyl ether monomers or polymers can also be used. Nonlimiting examples of acidic groups include carboxylic acid groups, sulfonic acid groups, halogenated alcohol groups, phenolic OH groups, and acidic OH groups.

Nonlimiting examples of polymers with basic side groups that can be reacted with anions include poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Nonlimiting examples of basic side groups include amino and imino groups.

As used herein, a "gelling agent" is any agent that cross-links a hydrogel precursor to form a hydrogel. For example, a gelling agent can cross-link the hydrogel precursor via covalent, ionic, or hydrogen bonds to form a hydrogel. For example, a water soluble polymer with charged side groups can be ionically crosslinked by reacting the polymer with an aqueous solution containing a gelling agent of opposite charge, e.g., a multivalent ion of the opposite charge. In some embodiments, the polymer has acidic side groups and the gelling agent is a multivalent cation. In other embodiments, the polymer has basic side groups and the gelling agent is a multivalent anion. In some embodiments, the gelling agent is a cation, e.g., $Pb^{2+}$, $Ba^{2+}$, $Fe^{3+}$, $Al^{3+}$, $Cu^{2+}$, $Cd^{2+}$, $Ho^{3+}$, $Ca^{2+}$, $Zn^{2+}$, $Co^{2+}$, $Ni^{2+}$, $Mn^{2+}$, or $Mg^{2+}$, $Sr^{2+}$, $Gd^{3+}$, $Pb^{2+}$, $Ra^{2+}$, $Fe^{2+}$, $Pd^{2+}$, $Bi^{3+}$, $Hg^{2+}$, $Au^{3+}$, $Co^{2+}$, $Co^{3+}$, $Cr^{2+}$, $Cr^{3+}$, $Mn^{4+}$, $Pt^{2+}$, $Pt^{4+}$, $Sn^{2+}$, $Sn^{4+}$, $Ce^{3+}$, $Ce^{4+}$, $Ga^{3+}$, $V^{3+}$, or $Rh^{3+}$.

In other embodiments, the hydrogel is a temperature-sensitive hydrogel (such as MATRIGEL™ or collagen), and gelation is induced by raising the temperature of the substrate to an appropriate level (such as 37° C.). The temperature can be maintained by immersing the substrate within a solution at the appropriate temperature, e.g., in a culture medium suitable for a particular type of cell. Temperature-sensitive hydrogels are known in the art and available commercially.

Cells

An array described herein can be loaded with cells simultaneously with a cation solution and/or hydrogel polymer. In some embodiments, the array is loaded with cells after the cation solution and/or hydrogel polymer is contacted with the substrate.

Cells that can be grown in the paper-based cellular arrays can be any prokaryotic or eukaryotic cell. Such cells include, for example, bacterial cells (such as *E. coli*), insect cells, yeast cells, or mammalian cells (such as Chinese hamster ovary cells (CHO) cells, COS cells, VERO cells, BHK cells, HeLa cells, Cv1 cells, MDCK cells, 293 cells, 3T3 cells, or PC12 cells). Other exemplary cells include cells from the members of the genus *Escherichia, Bacillus, Lactobacillus, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Schizosaccharomyces, Yarrowia,* or *Streptomyces*. Other cells include CD90+/CD45− hepatic tumor stem cells. In certain instances, the cells can be transformed or transfected with one or more expression vectors or viral vectors.

Multilayered Cellular Arrays

In certain embodiments, multi-layer paper-based cellular arrays can be fabricated. Such arrays can be produced by stacking layers of any three-dimensional cellular arrays described herein. For example, two or more paper arrays, each permeated with cell-containing hydrogels, can be stacked to produce a multi-layer array. In one or more embodiments, one or more paper arrays containing cell-free hydrogels can be overlaid with one or more cell-containing paper arrays to arrive at a multi-layer array. In one or more embodiments, one or more of the layers can contain an agent, e.g., a chemical agent, e.g., a chemoattractant. For example, a number of hydrogel-containing sheets can be stacked on top of a chemoattractant-containing sheet, and a cell-containing sheet can be placed on top of the stack.

Assays

Any cell-based assay known in the art can be performed using the three-dimensional cellular arrays described herein. For example, the three-dimensional cellular arrays described herein can be used in screening for agents that influence cell function, such as cell viability, apoptosis, proliferation, migration, and gene expression. Test agents can be added to the cellular arrays, can be adsorbed or covalently attached to the hydrogel or substrate (e.g., paper), or can be also included in a biodegradable matrix coated on the substrate (e.g., paper).

In some instances, a three-dimensional cellular array is contacted with a test agent and the cellular characteristic of interest, e.g., viability, apoptosis, proliferation, migration, or gene expression, is determined using, e.g., an assay described herein. A change in the cellular characteristic of interest in the presence of the test agent relative to a control (e.g., the absence of the test agent) is indicative that the test agent modulates cellular function.

In certain situations, the test agents are contained within wells, e.g., wells of a microtiter plate, and a three-dimensional cellular array is contacted with the test agents in the wells. For example, the test agents can be present in culture medium within the wells of a microtiter plate, and the cellular arrays can be contacted with, e.g., submerged into, the culture medium containing the test agent. In some instances, cellular characteristics can be measured before and after contacting the cellular array with the test agent. In some embodiments, a cellular array can be cut into segments (e.g., strips, cubes, disks, spheres), and a segment can be placed in each well of a microtiter plate.

Multi-layer paper-based arrays can be utilized for analyzing various cellular characteristics, such as migration, assembly, and proliferation. For example, stacked layers can be used for liquid guidance in three dimensions (Martinez et al., Proc Natl Acad Sci USA. 105:19606-11 (2008)).

In some embodiments, stacks of paper-based arrays can be used as a platform for migration assays. Diffusion gradients of oxygen and nutrients can be established in the multi-layer stack system. Hence, the same assay format provides a convenient system to model the environment in the interior of the solid tumors. In some embodiments, sheet-to-sheet migration of endothelial cells, endothelial progenitor cells (EPCs) (Asahara et al., Science 275, 964-967 (1997)), and breast cancer cells towards angiogenic factors, towards nutrients, oxygen or towards a chemoattractants can be investigated. For example, stacking of sheets that contain breast cancer cells in MATRIGEL™ and sheets that contain MATRIGEL™ without cells can be used to investigate invasion of cells into "blank" MATRIGEL™ containing sheets. Specific order of cell containing and "blank" stacks can be chosen to study direction of such migration (see FIG. 16).

In other embodiments, hypoxia-induced proliferation, differentiation or apoptosis of cells located at different depths (layers) can be easily quantified when stacked sheets are disassembled. Both migration and hypoxia assays can be used in high-throughput screening.

FIG. 6 illustrates an exemplary method in which a sheet of paper seeded with fluorescently-labeled cells is stacked on layers of hydrogel-containing sheets, which are then stacking on a paper that contains cell-adhesive hydrogel plus chemoattractant.

Figures 6A, 6B:
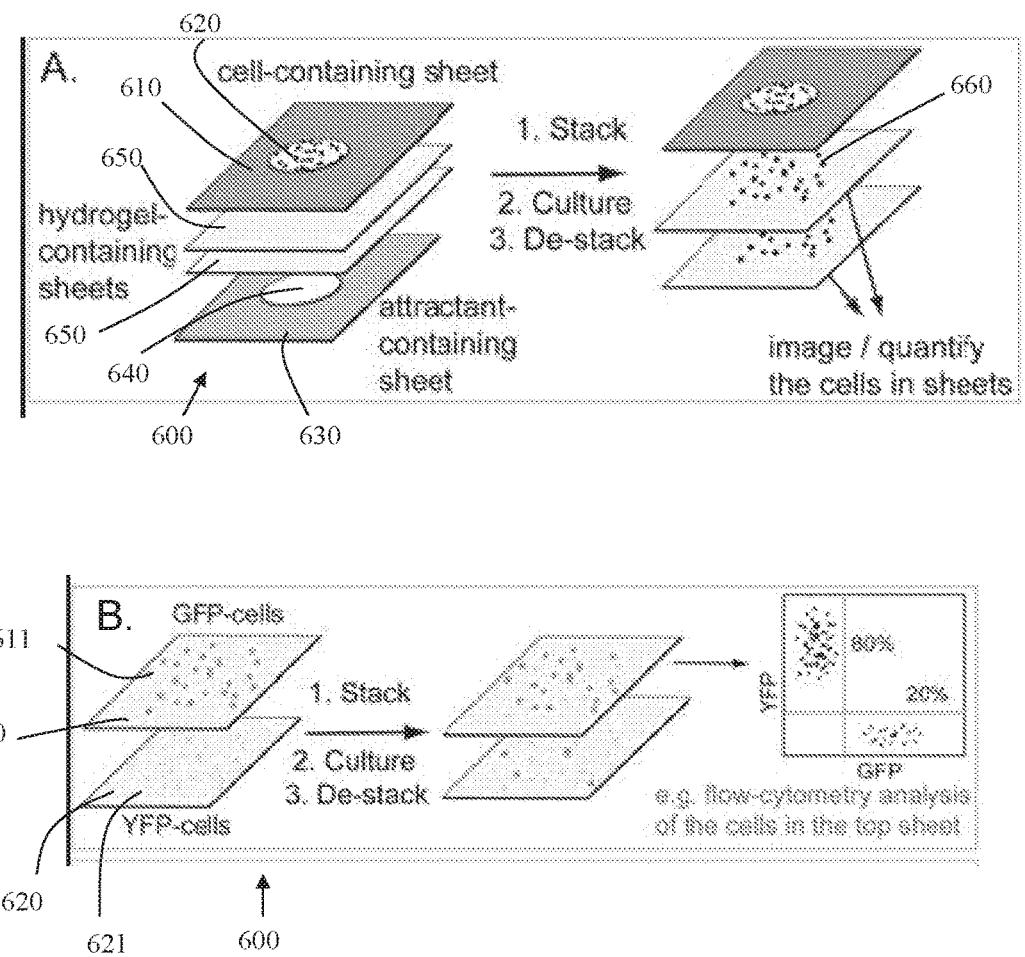
FIG. 6A depicts schematics of the investigation of cell migration.
FIG. 6B depicts cross-migration and invasion.

FIG. 6A is a schematic illustration of a multilayered cellular array 600. The array 600 includes a porous, hydrophilic substrate 610 containing cell-containing wells 620. Array 600 also includes a porous, hydrophilic substrate 630 having wells 640. Wells 640 can be pretreated with an agent of interest, e.g., an agent to be used to screen for cell behavior. Array 600 also includes intervening sheets 650. Intervening sheets 650 are porous, hydrophilic substrates that can include a hydrogel disposed within the intervening sheets 650. Array 600 is stacked such that the hydrophilic substrate 610, intervening sheets 650, and hydrophilic substrate 630 are in fluid contact. Array 600 is placed in a suitable culture medium in suitable conditions for cell growth. Array 600 is then destacked, and the number of cells 660 within hydrophilic substrate 610, intervening sheets 650, and hydrophilic substrate 630 is determined.

FIG. 6B is a schematic illustration of another multilayered cellular array 600. As depicted in FIG. 6B, array 600 includes porous, hydrophilic substrates 610 and 620, where hydrophilic substrate 610 contains a hydrogel containing cell type 611, and hydrophilic substrate 620 contains a hydrogel containing cell type 621. The hydrophilic substrates 610 and 620 are stacked, placed in cell culture medium, and then destacked. The number of cell type 611 and cell type 621 in hydrophilic substrates 610 and 620 are analyzed.

In particular embodiments, upon destacking, the cells in the separated stacks of paper remain viable and they can be cultured separately or characterized using any assays described herein to compare the cells in separate stacks of paper. For example, viable cells in each sheet can be quantified, using cell proliferation reagents (e.g., Alamar Blue) or fluorimetric assays (e.g., calcein stain, FIG. 15). Cells in each layers can be fixed and quantified with fluorescent labeling agents (e.g. SYTOX to label DNA, Phalloidine to label F-actin, FIG. 15). Cells in each sheet can be lysed, and this lysate can be used to measure the level of expression of genes of interest (e.g. VEGF and IGFPB3, FIG. 15) or to measure the cellular concentration of specific proteins (e.g. hypoxia induced factors (HIF) 1 and 2 with commercial ELISA kits). Cells can be enzymatically removed from each sheet and characterized by flow-cytometry analysis to assess the number of live, apoptotic, and necrotic cells and to perform cell cycle analysis of cell population in each sheet. Fluorescent reporters or cell tracer dyes can be used to label the cells in each sheet and to trace the origin of each cell in each layer (FIG. 6B). Finally, comparative transcriptome profiling of cells isolated from different layer sheet can provide novel insight on transformations that occur in the interior of solid tumors and other non-vascularized three-dimensional structures composed of multiple layers of cells.

In some embodiments, co-culture of cells in stacked sheets of paper can be used to investigate self-assembly of tissue-tissue interfaces, cross-migration of cells, and hypoxia responses in a tissue-like environment. For example, three-dimensional cell cultures on paper can be used to investigate the interaction of cells with surrounding tissues, which can be critical for vascular network formation and delivery of nutrients to organs and tumors. The microenvironment formed by endothelial cells can also be examined, which is also critical for proliferation and differentiation of multiple cell types.

Figure 6C:
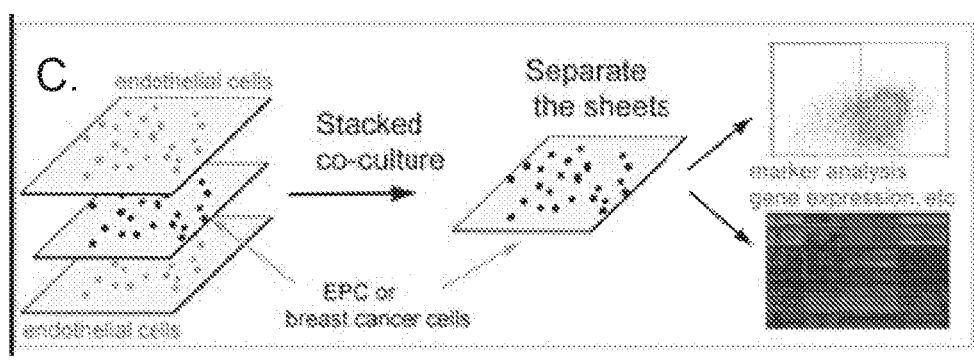
FIG. 6C depicts three-dimensional co-culture using three-dimensional cellular arrays of stacked sheets of papers permeated with cell-containing hydrogels.

Paper arrays that contain cells can be stacked with arrays that contain other cell types to produce a co-culture (see, e.g., FIG. 6C). Responses of both cell types in this sheet co-culture can be readily investigated after the sheets are disassembled. For example, stacked arrays of co-cultures of endothelial cells and breast cancer cells can be used to study tissue ingrowth (e.g., metastases, tumor vascularization). More specifically, cross-migration of cells between the sheets that contain endothelial cells and tumor cells can be performed using reporter cell lines (FIG. 6B). The number of cells in each layer prior and postmigration can be quantified as described above.

In another example, endothelial progenitor cells (EPCs) can be cocultured with endothelial cells and breast cancer cells in multi-layered three-dimensional cellular arrays. EPCs in vivo are known to interact with vascular endothelium and undergo transendothelial migration as a first step of homing to ischemic or injured tissue. Conversely, EPC-secreted factors enhance vascularization and promote migratory response in pre-existing endothelial cells (Urbich, et al., Circ. Res. 95:343-353 (2004)). EPCs can be plated in paper-based matrices and then stacked with layers that contain endothelial cell and breast cancer cells to investigate long-term responses in endothelial-EPC co-culture. Cross-migration of these cells in response to angiogenic factors and oxygen concentration gradient can be investigated. Expression profiling and flow cytometry analysis of the EPC and co-cultured cell types can be used to characterize their differentiation state (FIG. 6C).

In other instances, "multistacks of bacteria" can be used to analyze bacteria grown in various conditions. For example, multilayer stacks of bacteria can be used as a model for bacterial biofilms, which are three-dimensional structures containing multiple layers of bacteria. Bacteria in various layers of a biofilm are exposed to different conditions, such as different amounts of nutrients or oxygen. Bacteria grown in paper and stacked can be used to model the nutrient/oxygen rich and restricted regions present in biofilms. Analysis of the biochemical composition of bacteria in different layers can be used to understand the transformation of bacteria that occur during biofilm formation. It is known in the art that oxygen/nutrient starvation within biofilms can potentially induce bacteria to acquire specific phenotypes that exhibit more or less susceptibility to various cytotoxic agents (K. Lewis, Nat Rev. Microbiol. 2007, 5, 48-56). Thus, analyzing bacterial survival in different layers of a multi-layer cellular array upon treatment with different test agents can be useful to identify agents to treat bacterial biofilms.

Figures 17A, 17B, 17C:
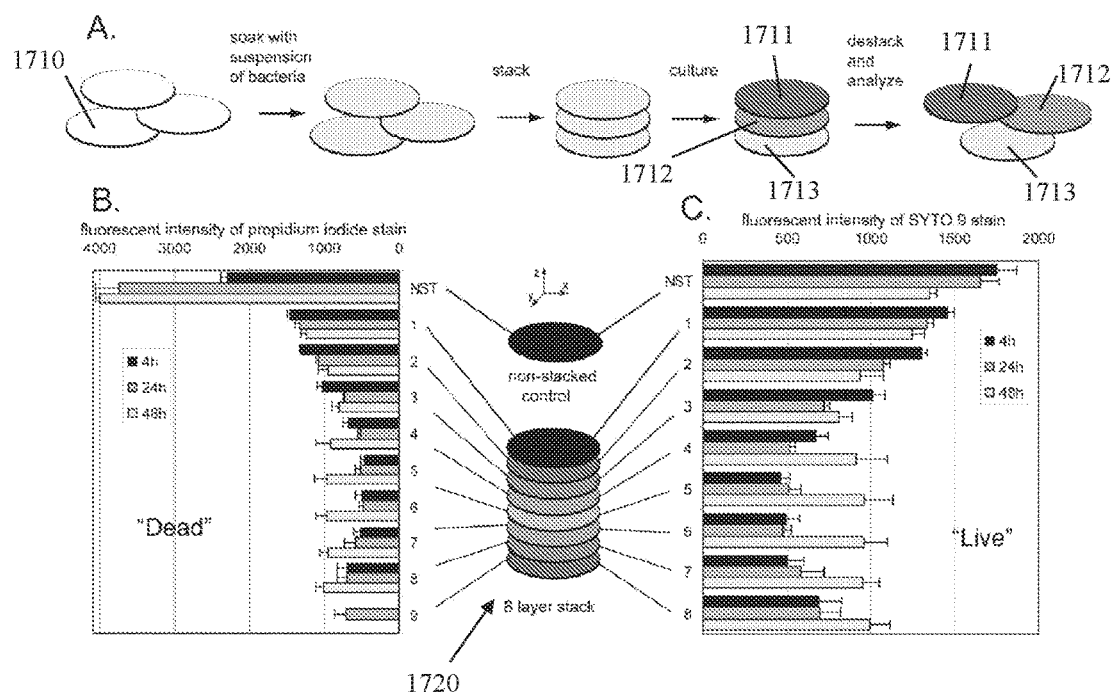
FIG. 17A is a schematic illustrating the use of stacked three-dimensional cellular arrays to analyze bacterial cultures.
FIG. 17B is a graph of the number of dead *Pseudomonas aeruginosa* PA14 cells in various layers.
FIG. 17C is a graph of the number of live *Pseudomonas aeruginosa* PA14 cells in various layers.

One exemplary system is illustrated in FIG. 17, in which bacteria in the multi-layers of paper are in oxygen/nutrient accessible (layer 1 and 8) or restricted layers (layers 2-7). As depicted in FIG. 17A, porous, hydrophobic substrates 1710 are soaked in a suspension of bacteria. The substrates 1710 are stacked and cultured. The substrates are destacked and the growth of bacteria in layers 1711, 1712, and 1713 are analyzed. FIG. 17B depicts the analysis of dead and live bacteria from a stack 1720 that included layers 1, 2, 3, 4, 5, 6, 7, and 8.

High-Throughput Screening

The three-dimensional cellular arrays described herein can be used for high-throughput screening methods, for example, to screen for modulatory agents. In some embodiments, patterned paper (e.g., patterned into hydrophilic and hydrophobic regions) can be spotted with one or more potential modulatory agents. The patterned paper can then be overlayed with a three-dimensional cellular array, the modulatory agent(s) can diffuse into the array, and the effect of the modulatory agents on the cells within the array can be assessed.

Figures 7A, 7B, 7C:
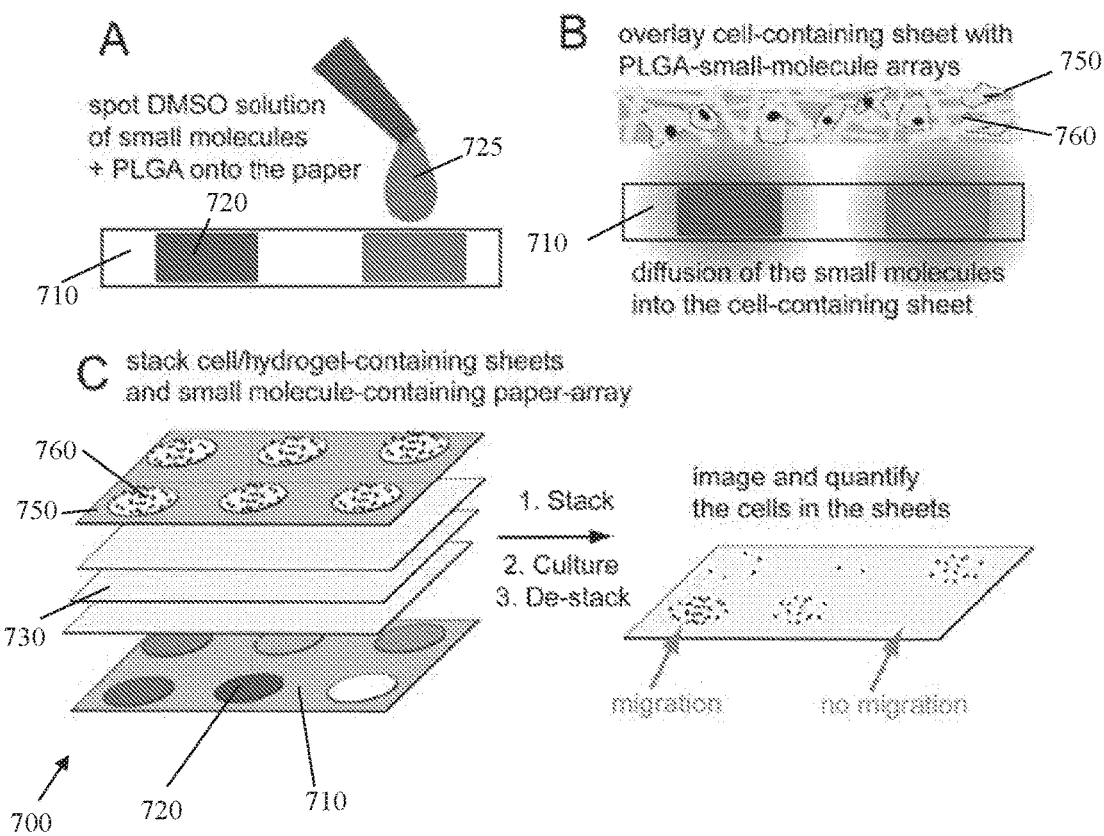
FIGS. 7A, 7B, and 7C are schematics depicting the integration of layered assays and high-throughput screening for small molecules that affect proliferation and migration of cells in three-dimensional growth substrates.

FIG. 7 illustrates an exemplary screening method. Cell-based high-throughput screening is performed using localized release of small molecules from paper arrays of biodegradable polymers (e.g., poly-lactic glycolic acid, PLGA) (Bailey, et al., Proc. Natl. Acad. Sci. U.S.A. 101:16144-16149 (2004)). In this method, a paper patterned with small molecules in PLGA is overlayed with a cellular array (FIG. 7B). The effect of the diffusion of the small molecules on the cells within the array is analyzed.

As depicted in FIG. 7A, porous, hydrophilic substrate 710 includes areas or "wells" 720 within the substrate 710. The wells 720 are formed by contacting an aqueous solution 725 of a particular agent onto substrate 710. As depicted in FIG. 7B, a porous, hydrophilic substrate 750 that includes cell-containing three-dimensional hydrogel 760 is stacked on top of substrate 710, allowing the agent to diffuse into substrate 750. The effect of the agent on cellular activity can be determined In other embodiments, a high throughput screen includes a multi-layer paper-based array. For example, a sheet of paper patterned with small molecules can be stacked onto a number of sheets of paper, one of which is a three-dimensional cellular array. The effect of the small molecules on a cellular property, such as cell migration, can be assayed. An exemplary method is depicted in FIG. 7C.

FIG. 7C depicts multilayered cellular array 700. Array 700 includes hydrophilic substrate 750. Substrate 750 includes "wells" of cells within a three-dimensional hydrogel 760. Array 700 also includes hydrophilic substrate 710, which includes "wells" 720 within the substrate 710. The wells 720 include particular agents within substrate 710. Array 700 also includes intervening porous, hydrophilic sheets 730. Hydrophilic substrate 710, which includes "wells" 720 within the substrate 710. The wells 720 include particular agents within substrate 710. Array 700 also includes intervening porous, hydrophilic sheets 730. Substrate 710, intervening sheets 730, and substrate 760 are stacked, cultured, destacked, and the number of cells in substrate 710, intervening sheets 730, and substrate 760, is determined. In particular embodiments, the number of cells at a particular location on substrate 710, intervening sheets 730, and substrate 760 is used to identify an agent 720 from substrate 710 that influences cell behavior, e.g., migration, proliferation, or death.

In some embodiments, high-throughput screening can be performed by placing cell-containing three-dimensional paper arrays into microtiter plates. Each well of the microtiter plate can include an agent to be screened, and the responses of the cells within the arrays can be assayed.

Figures 8A, 8B:
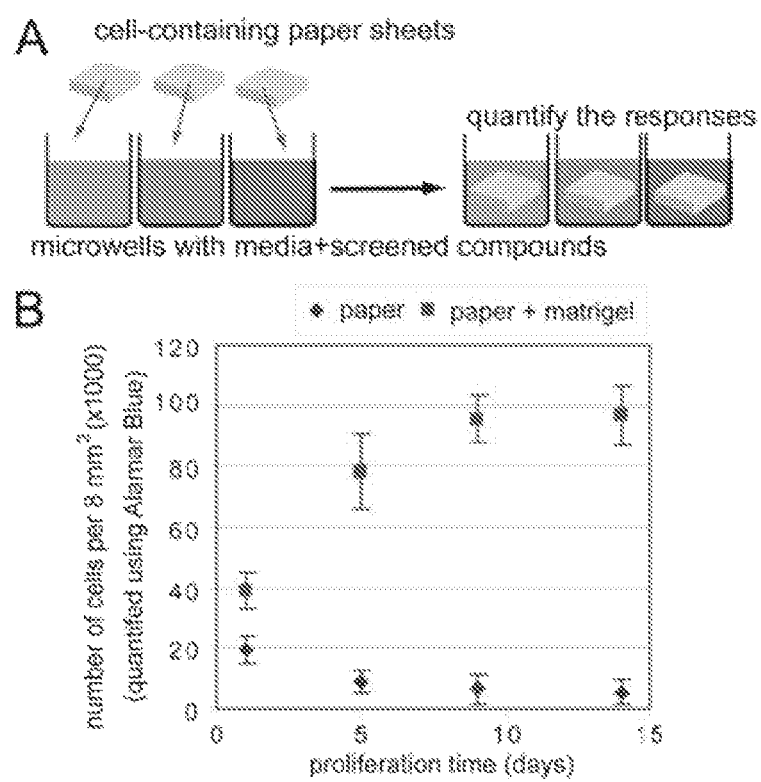
FIG. 8A is a schematic depicting the integration of a microwell screening format and three-dimensional cellular arrays.
FIG. 8B is a graph of the proliferation of 3T3 cells in paper or paper with MATRIGEL™.
Figure 9:
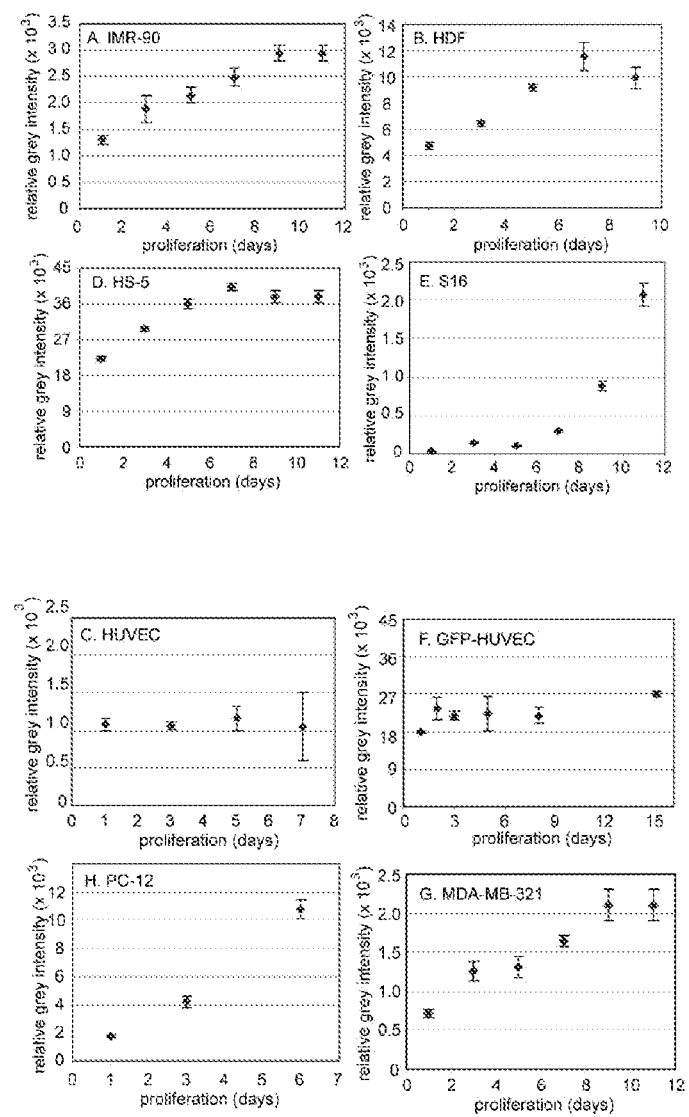
FIG. 9 depicts graphs and confocal images of various cell types grown in three-dimensional cellular arrays containing MATRIGEL™. 4 µL (FIGS. 9A-9D) or 1 uL (FIGS. 9E-9H) of suspension of cells in MATRIGEL™ ($10^7$ cells/mL) were spotted onto the plain filter paper and the paper was suspended in the appropriate culture media. At the indicated time point, the cellular arrays were removed from the media and fixed with formaldehyde. At the end of the time course, all samples were stained with fluorescently labeled phalloidin and quantified using fluorescent gel scanner and ImageJ. Each data point is an average from 4 measurements; the error bar is equal to one standard deviation.

One exemplary method is depicted in FIG. 8. In this method, a paper array of the same size is distributed to each well of the microtiter plate to ensure delivery of nearly identical number of cells per well (FIG. 8A). To illustrate this strategy, 2 mm×4 mm pieces of filter paper were permeated with suspension of 3T3 fibroblasts in MATRIGEL™ and then distributed into the wells of a 96-well plate. Alamar Blue was used to estimate the number of cells. Less than 10% deviation was observed for measurements from 8 independent wells, confirming that a similar number of three-dimensional-array embedded cells was delivered to the wells. 3T3 cells proliferated within MATRIGEL™-soaked paper but not within the MATRIGEL™-free paper (FIG. 8B), and this proliferation was halted when colchicine was added to the wells. This system, therefore, can be used to screen for agents that influence proliferation of cells in three-dimensional arrays.

Figure 18:
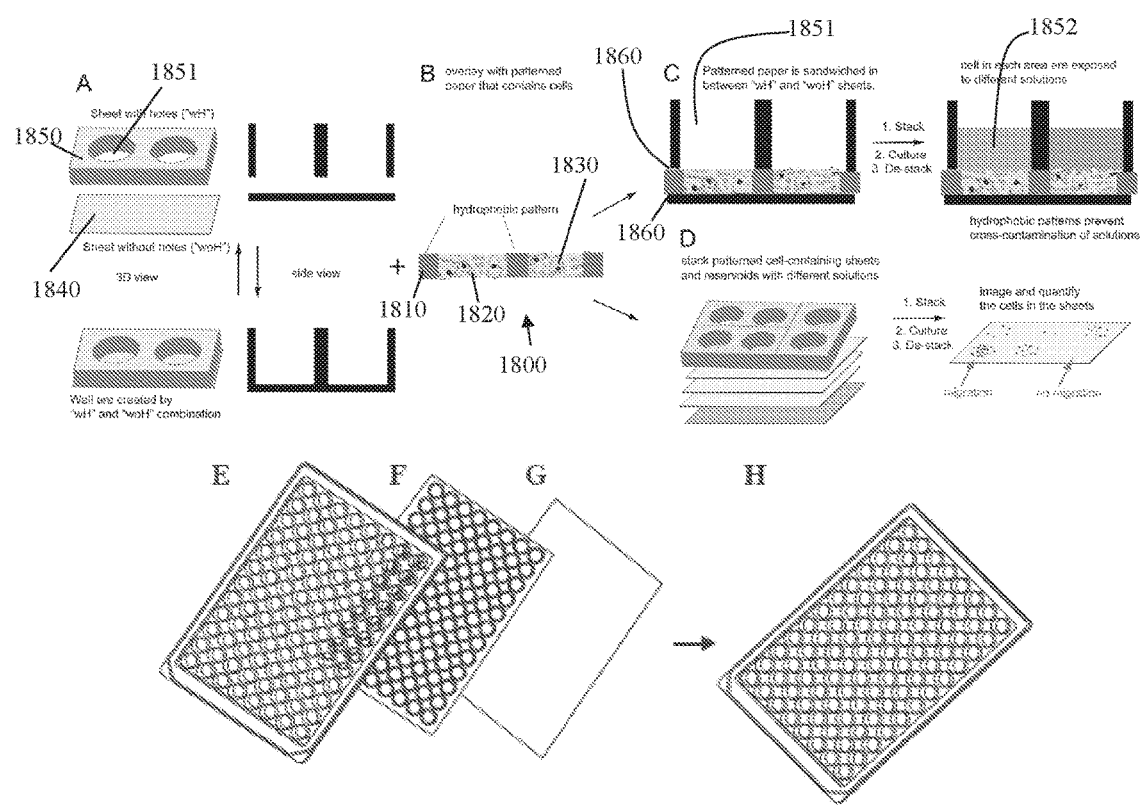
FIG. 18A is a schematic of a plate with wells that can be created by stacking a sheet of material with holes ("wH") and without holes ("woH").
FIG. 18B is a schematic of cells seeded on patterned paper that can be sandwiched in between the "wH" and "woH" sheets depicted in FIG. 18A.
FIG. 18C depicts a system containing a layer of cell-containing patterned paper. Cells in the paper in different "wells" can be exposed to different solutions.
FIG. 18D is a schematic illustrating a migration assay.
FIG. 18E depicts a bottomless 96-well plate.
FIG. 18F depicts paper patterned into hydrophobic and hydrophilic regions.
FIG. 18G depicts a flat bottom surface.
FIG. 18H depicts a combination of the components depicted in FIGS. 18E, 18F, and 18G, resulting in a 96-well platform where each well contains a layer of paper and where each well can be exposed to a different solution.

Another exemplary method is depicted in FIG. 18. In this method, a paper array 1800 patterned into hydrophobic 1810 and hydrophilic 1820 regions is embedded with cells in a hydrogel 1830. The patterned paper 1800 is then contacted with two sheets 1840 and 1850 of water-impermeable material. One sheet 1850 with through holes (designated as "wH") forms wells 1851 that contain the liquid, the other sheet 1840 without holes (designated as "woH") forms the bottom of the wells. The hydrophobic boundaries 1820 of the patterned paper 1800 create water-impervious seals 1860 that prevent capillary wicking of fluids between separate wells 1851. The wells 1851 can then be exposed to different solutions or agents 1852 and the effect on the cells can be analyzed.

Sheets 1840 and 1850 designated "wH" and "woH" above can be used to create screening arrays without limitation to the size, shape, or features of the plate; to the size, shape, or number of holes (wells); or to the materials and methods used to prepare the plate. These sheets can be made by injection molding, casting, machining, laser cutting, or vacuum sheet forming one or more resins. The sheets can be made from transparent or opaque materials; material can be metal, platic, glass, ceramic and other water-impermeable material that is, preferably, non-toxic to cells. In particular embodiment, sheet 1850 designated "wH" can contain an ordered array or holes to create an ordered array of well that can be recognized by instruments which are designed to work with standard microwell plates (e.g., 12×8 array of holes in "wH" can be used to create an array that has a layout identical to 96-well plate). In a particular embodiment, the sheet 1850 designated "wH" with specific patterns of holes can be obtained as commercially available bottomless 96-, 384-, 1536-, and 3456-well plates (e.g., from Greiner Labortechnik of Frickenhausen, Germany; and Corning Life Sciences of Acton, Mass.).

Any of the multi-layer assays described herein can be adapted to be used with a bottomless microtiter plate. For example, multiple layers of patterned paper can be stacked and contacted with "wH" and "woH" sheets (as depicted in FIG. 18D), and each layer can contain various agents or can be used in, e.g., migration assay analysis.

In particular embodiments, three-dimensional cellular arrays are used in a high throughput screening using normal or malignant cells and modulatory agents to identify those that promote (or inhibit) cell death, proliferation, migration or differentiation. If multiple layers of paper are used as described herein, cell death, proliferation, migration or differentiation in different layer in response to modulatory agent can be assessed.

In other embodiments, three-dimensional cellular arrays are used for high throughput screening using progenitor and stem cells. To date, high-throughput screening of stem and progenitor cells has been performed on two dimensional substrates, and these methods can be extended using the cellular arrays described herein. Three-dimensional layers of cells inside the paper arrays mimic the three-dimensional aggregates of cells that are commonly used for growth or differentiation of progenitor and stem cells. For example, three dimensional aggregate of embryonic stem cells (ESCc) termed "embryo bodies" are used for differentiation of ES cells, three dimensional aggregates of neural stem cells (NSCs) termed "neurospheres" are used for proliferation and differentiation of neuronal stem cells. In particular embodiment, cellular arrays can be plated with ESCs or NSC and one or multiple layers of these arrays can be used to create an array of three-dimensional structure similar to "embryo bodies" or "neurospheres". Differentiation inside such structures can be investigated when the layers of the array are separated. Screening for "modulatory agents" that regulate this differentiation can be performed using any of the methods described herein.

High-Throughput Screening of 3D Cultures of Different Geometry

Paper-supported arrays can be used in a screening procedure that involves rapid generation of 3D cultures of different geometries and investigation of how the properties of the cells (e.g., metabolic activity, growth, migration, differentiation) are influenced by 3D geometry. Different geometries can be exemplified by (but not limited to): (1) 3D cultures of physical different size or shape. These cultures can be generated by stacking different number of sheets and sheets that contain holes of defined size in defined location. Planar arrangement of holes and vertical arrangement of sheets determines the resulting 3D size and shape of the culture (see, e.g., FIG. 19); (2) 3D-cultures that have specific mechanical properties in specific locations. These cultures can be generated by stacking sheets of different mechanical properties; the order of the sheets in the stack determines the spatial location of mechnical properties in vertical direction; (3) 3D-cultures that have specific chemical composition in specific location. These cultures can be generated by stacking sheets that contain cells encapsulated in different hydrogels in different areas of the sheet, the order of the sheets in the stack determines the spatial location of chemical properties in vertical direction. Combination of lateral patterning and stacking allows controlling chemical composition in X, Y and Z.

The three examples above are independent and can be used as a combination. For example, a stack of perforated papers can present some areas that have different mechanical properties, and can also include some areas that have cells encapsulated in hydrogels of different composition.

Types of Cellular Assays

The three-dimensional arrays described herein can be used to characterize various properties of cells grown within the arrays. For example, qualitative and quantitative detection of cells in paper based arrays is possible, such as using fluorescent microscopy or colorimetric assays known in the art.

Certain embodiments will employ conventional techniques of molecular biology (including recombinant techniques), microbiology, cell biology, biochemistry, and immunology, which are known to those of ordinary skill of the art. Such techniques are described in, e.g., "Molecular Cloning: A Laboratory Manual", third edition (Sambrook et al., 2001); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Apoptosis Assays

Any standard assay for measuring apoptosis known in the art can be used to determine the apoptosis of cells in three-dimensional cellular arrays described herein. Such assays include, without limitation, the terminal deoxynucleotidyl transferase-mediated digoxigenin-11-dUTP nick end labeling (TUNEL) assay (Lazebnik et al. 1994, Nature 371, 346); the incorporation of fluorescein-dUTP (Yonehara et al., 1989, J. Exp. Med. 169, 1747); acridine orange staining (Lucas, R., et al., 1998, Blood 15:4730-41); the caspase-3/7 assay (available as Apo-ONE™ Homogeneous Caspase-3/7 assay from Promega, cat#67790); and the cell death nucleosome ELISA assay (available from Roche, Cat#1774425).

In some instances, a test agent can be added to a three-dimensional cellular array described herein and changes in induction of apoptosis relative to controls (where no test agent is added) can be used to identify candidate agents to modulate apoptosis.

Cell Proliferation and Cell Cycle Assays

The proliferation of cells within three-dimensional cellular arrays described herein can be assayed using any method known in the art. Known methods include, without limitation, bromodeoxyuridine (BRDU) or 5-ethynyl-2'-deoxyuridine (EdU) (FIG. 15) incorporation assays (Hoshino et al. 1986, Int. J. Cancer 38, 369; Campana et al., 1988, J. Immunol. Meth. 107, 79; Click-iT® EdU, Invitrogen); phospho-histone H3 staining (Chadlee, D. N. 1995, J. Biol. Chem 270:20098-105); $^3$[H]-thymidine incorporation (Chen, J., 1996, Oncogene 13:1395-403; Jeoung, J., 1995, J. Biol. Chem. 270:18367-73); metabolic activity measurement using Alamar Blue assay (FIG. 15) (available from Biosource International); (Voytik-Harbin S L et al., 1998, In Vitro Cell Dev Biol Anim 34:239-46), Calcein assays (FIG. 15) (available from Invitrogen) or CellTitelGlo assays (available from Promega). The signal produced by specific assay (fluorescence, chemiluminescence, radioactivity) emanates from areas that containe(d) cells and it can be measured using any conventional method (fluorescent microscope, fluorescent or luminescence scanner, phosphorimager, gel imager, etc).

Biochemical Assays

The level of gene expression can be analyzed using the three-dimensional cellular arrays described herein. For example, cells can be lysed directly within a cellular array and the lysates can be used in standard assays known in the art, e.g., Northern analysis, ribonuclease protection assays, or reverse transcription-polymerase chain reaction (RT-PCR) (see, e.g., Sambrook et al., Molecular Cloning: A Laboratory Manual (3$^{rd}$ ed. 2001)).

Changes in gene expression in cells grown in three-dimensional arrays can be assayed using known genome-wide analysis techniques. For example, an Affymetrix GeneChip® can be used to perform transcriptome analysis; Illumina Deep Sequenceing can be used to perform the analysis of coding and regulatory RNAs (e.g. micro RNA or miRNA) Gene expression and regulatory RNA profiles can be compared to known profiles for cells grown ex vivo and in vivo.

The cellular material obtained from the cells cultured in three-dimensional cellular arrays can also be used to analyze protein levels, by methods such as by Western analysis or immunoassays. Proteins, carbohydrates and metabolites from the cellular material can be analyzed by known global profiling methods such as those based on mass spectrometry (e.g. shotgun proteomics, metabolomics) or NMR spectroscopy (metabonomics).

Analysis of Isolated Cells

The cells can be isolated from the three-dimensional cellular arrays described herein and used in subsequent assays. For example, isolated cells can be used in flow-cytometry analysis. Cells can be isolated from the arrays using any known method, e.g., enzymatically. One exemplary enzyme is reactive to cellulose substrates, such as cellulase from *Trichoderma reesei*.

Responses to External Stimuli

Cells grown in three-dimensional cellular arrays can be evaluated for response to known effectors, e.g., effectors of proliferation and morphogenesis. In one exemplary assay, the responses of endothelial cells (e.g., tube and lumen formation) can be evaluated. These responses are known to be regulated by Integrin-ECM interactions and the downstream Rho GTPase-mediated pathways; and a panel of small-molecules and siRNA known to inhibit these processes can be readily obtained and tested (Koh, et al., J. Cell Sci. 121:989-1001 (2008); Ghosh, et al., Proc. Natl. Acad. Sci. U.S.A. in press, doi: 10.1073/pnas.0800835105 (2008)). Test Agents The three-dimensional cellular arrays described herein can be used to assay any test agent. A "test agent" can be any agent, such as a small organic or inorganic molecule, amino acid, polypeptide, nucleic acid, peptide nucleic acid, carbohydrate, or polysaccharide. The test agents can be synthetic, naturally occurring, or a combination of synthetic and natural components. In some embodiments, the test agent can be a member of a library of test agents (e.g., a combinatorial chemical library) or a component of a cellular extract or bodily fluid (e.g., urine, blood, tears, sweat, or saliva).

The invention is further illustrated by the following examples. The examples are provided for illustrative purposes only. They are not to be construed as limiting the scope or content of the invention in any way.

EXAMPLES

Example 1—Morphology and Growth Rates of Cells within MATRIGEL™-Permeated Paper

The long-term growth rates of several cells grown within three-dimensional matrices of paper permeated with MATRIGEL™ were tested. These cells included primary cells (human umbilical vein endothelial cells (HUVEC), human dermal fibroblasts (HDF), IMR-90 human lung fibroblasts), immortalized cells (telomerase-transfected GFP-HUVEC, HS-5 human bone marrow stroma cells, S16 rat Schwann cells) and cancer cells (MDA-MB-231 human breast adenocarcinoma and PC-12 rat pheochromocytoma). (FIGS. 9A-G).

The population doubling time of most of the cells in paper-supported MATRIGEL™ matrix was significantly lower than their doubling time in 2D culture. The doubling time was the highest for S16 cells (~36 hours) and PC-12 cells (~48 hours), while both primary HUVECs and immortalized GFP-HUVEC cell lines exhibited little to no proliferation. These results agree with observations that many cell types suspended in three-dimensional hydrogels proliferate slower than the same cells plated on two-dimensional surfaces of the culture dishes.

Confocal microscopy was used to examine the morphology of cells in paper-supported MATRIGEL™ matrices. Human umbilical cord vascular endothelial cells (HUVECs) were used as a model system. HUVECs exhibit distinct morphological change in three-dimensional-cells form hollow structures reminiscent of capillary tubes in vivo. In contrast, HUVECs form flat cell monolayer when cultured on two-dimensional culture dishes. These cells are known to decrease their growth rate when encapsulated inside the three-dimensional matrices.

A suspension of HUVEC in MATRIGEL™ were spotted onto paper. In 7-12 days the cells formed hollow blood vessel-like structures. This observation confirmed that cells cultured in MATRIGEL™-permeated paper exhibit behavior characteristic of cells grown in three-dimensional matrices. Fibroblasts, stroma cells and Schwann cells spread out through the cellulose fibers, forming multilayer structures upon long-term proliferation. MDA-MB-231 cells exhibited little spreading and formed disorganized aggregates of cells. PC-12 cells cultured in paper permeated with MATRIGEL™ were induced to differentiate into of neuron-like cells that formed three-dimensional network of interconnected neurites.

Overall, paper did not have detrimental effects on the morphology and physiology of the primary and immortalized cells examined Example 2—Comparison of Gene Expression in Cells within MATRIGEL™-Permeated Paper and on Two-Dimensional Substrates Cells grown in paper are different from cells grown in two dimensions. Global gene expression profiling was used to investigate how similar cells grown in three dimensions on paper are to cells grown in three dimensions.

Gene expression levels in HUVECs proliferated on chemically identical two-dimensional and three-dimensional systems were compared. Cells cultured on two-dimensional MATRIGEL™ monolayers were compared to those cultured inside MATRIGEL™-permeated paper. Cells were lysed and processed to isolate total RNA. Seven candidate genes were analyzed for differential expression in cells grown in two-dimensional and three-dimensional systems.

Figure 10:
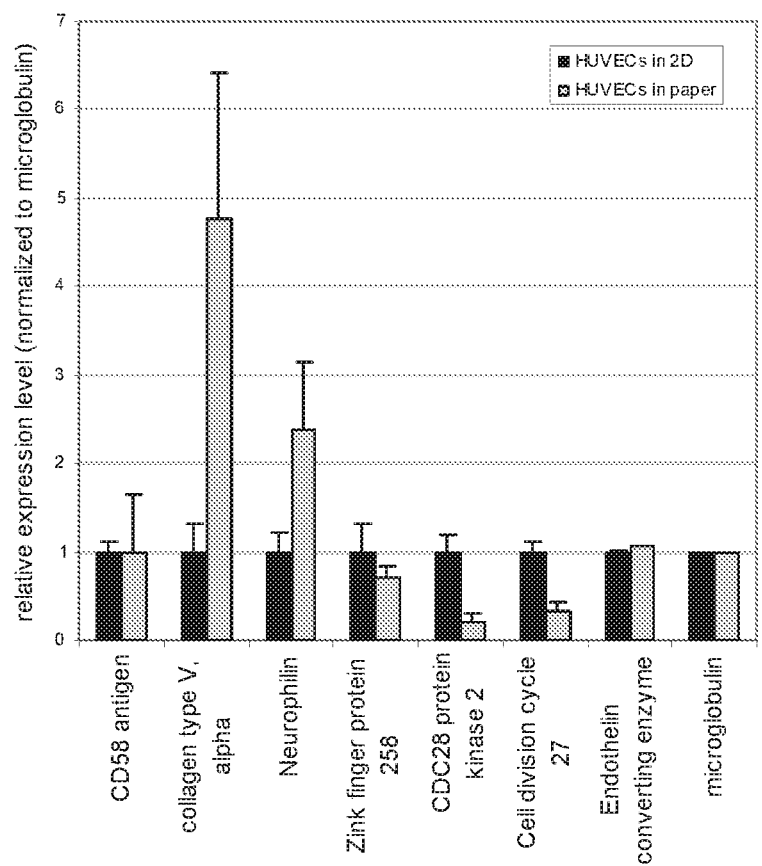
FIG. 10 is a graph of the relative expression levels of various genes in HUVEC cells on two-dimensional and three-dimensional paper cellular arrays.

Quantitative real-time PCR demonstrated that 4 out of 7 selected genes had different expression levels (see FIG. 10). Expression levels in cells on two-dimensional substrate were set to 1 for every gene; the plot shows relative up- or down-regulation of gene expression in cells in MATRIGEL™-permeated paper. Microglobulin was used as a reference gene for all samples. Linear region was used for every set of primers.

Example 3—Paper is a Convenient Platform to Study Three-Dimensional Migration of Cells Paper can be used to grow cells in three-dimensional and can subsequently be used to screen for responses in three-dimensional that do not occur in two-dimensional (or those responses are different in two-dimensional). To demonstrate this, paper was used as a platform to investigate three-dimensional migration and tube formation of endothelial cells (HUVEC).

Figures 11A, 11B:
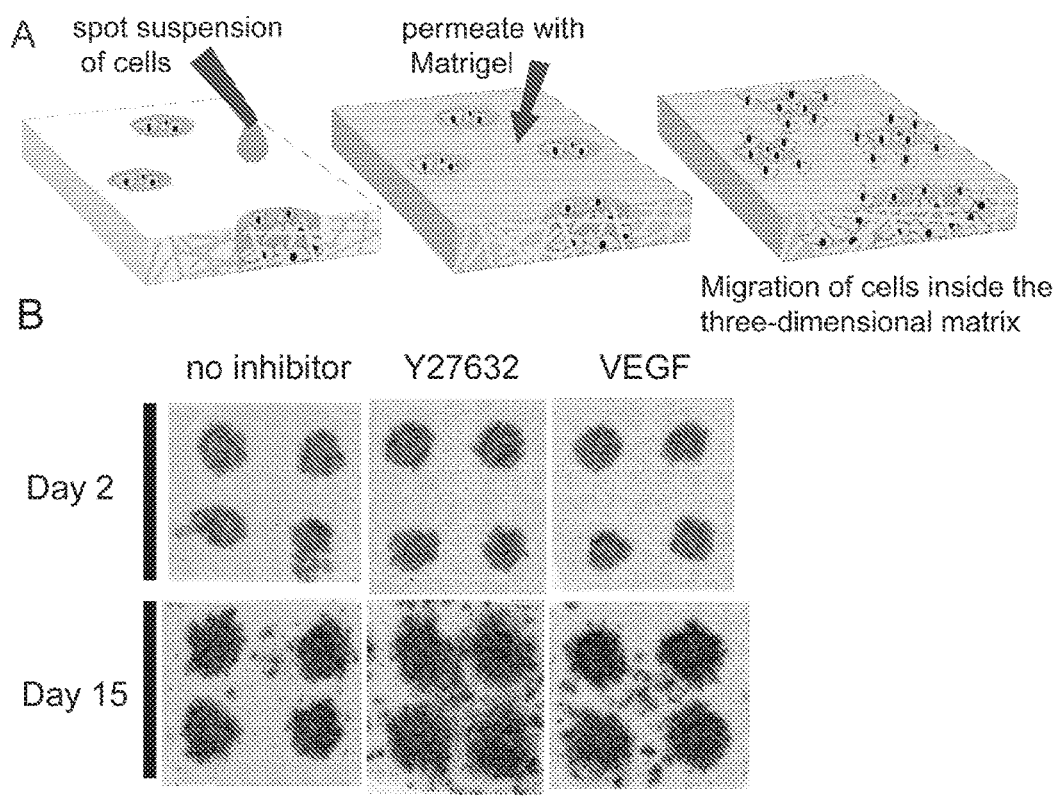
FIG. 11A is a schematic illustrating a two-step procedure for investigating the three-dimensional migration of HUVEC cells.
FIG. 11B are gel scanner images of the migration of HUVEC cells over time under various conditions.

A suspension of cells in MATRIGEL™ (1 µL, $10^7$ cells/mL) was spotted onto paper, and the paper was immersed in MATRIGEL™. This resulted in 2-3 mm circular patterns that contained cells in three-dimensional-matrix surrounded by cell-free three-dimensional matrix (see FIG. 11A). Migration of the cells into the surrounding MATRIGEL™ was monitored over time using a fluorescent gel scanner. Upon incubation in cell culture media, cells invaded the surrounding region (FIG. 11B). The radius of the cell-containing spot served as the measure of the migration.

Cell-containing sheets were suspended in endothelial culture media supplemented with 100 ng/mL VEGF ("VEGF") or 10 µM of small molecule inhibitor of Rho kinase Y27632 ("Y27632"). The samples were fixed and stained with SYTOX at the days indicated in FIG. 11B. Outgrowth of cells was promoted by Y27632, a small-molecule inhibitor of Rho kinase (ROCK). The radius of the invasion in complete endothelial growth media (EGM) or EGM with additional 100 ng/mL VEGF was significantly lower then that in EGM+10 µM Y27632 (FIG. 11B). Lumens and tube-like structures were observed in the "invaded regions".

In another embodiment, endothelial cells are spotted in the middle and breast cancer cells on the outside and co-cultured in three-dimensional. The cell types are differentially-labeled, and lateral cross-invasion of these two cell types are observed (representing a combination of "metastases" and "angiogenesis").

Example 4—Application of Paper in Cell-based High-throughput Screening

Paper-supported three-dimensional substrates can be readily utilized with existing high-throughput screening infrastructures. Paper permeated with a cell-hydrogel suspension were distributed to wells of a 96-well microplates. Distribution of paper pieces of the same size were used to control delivery of similar number of cells per well. High-throughput investigation of cellular responses in three-dimensional were performed using luminescence.

Specifically, a simple cell-based model system was used to produce a luminescent readout. Baby hamster kidney (BHK) cells were infected by vesicular stomatitis virus carrying a luciferase reporter pasmid (lux-VSV). Cells infected with this virus produce luciferase.

A suspension of BHK cells in MATRIGEL™ was permeated into 2×4 mm pieces of paper. These pieces were distributed to the wells of a 96-well plate, and the cells were incubated with growth media for 24 hours. An increasing titer of lux-VSV was added to the wells. 6 hours later, the media was removed, a solution of luciferin in cell lysis buffer was added to the wells, and the signal was read using a luminescence plate reader.

Figures 12A, 12B:
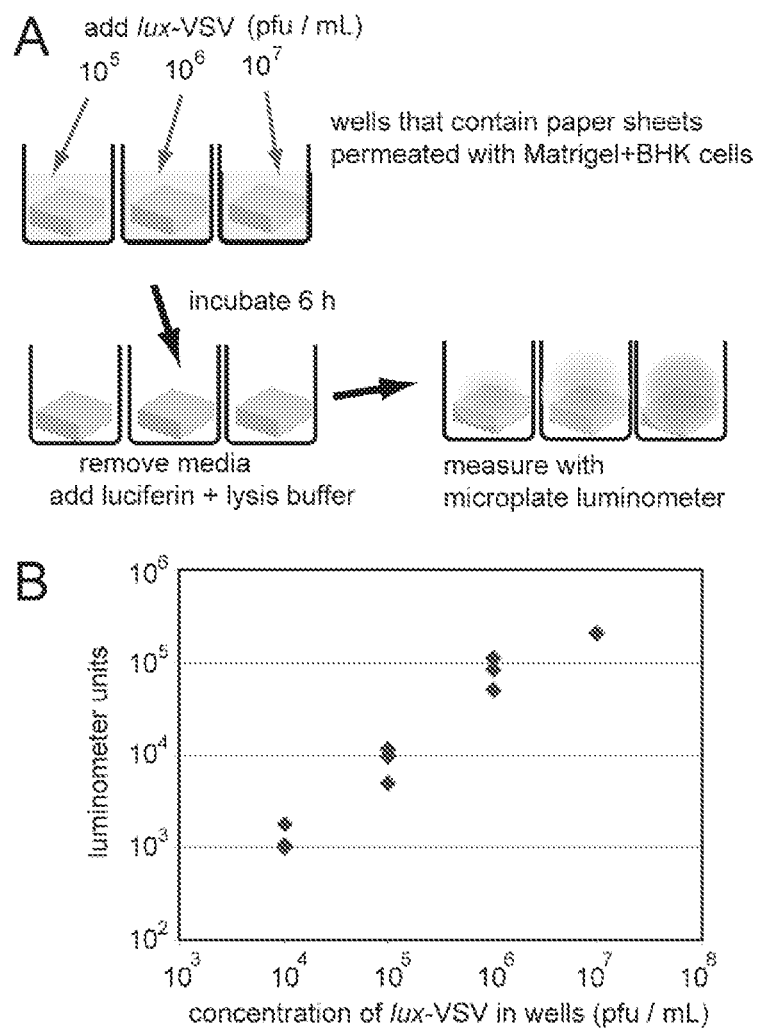
FIG. 12A is a schematic of a viral infection assay using BHK cell-containing paper and microtiter plates.
FIG. 12B is a graph of luminescent readout from a 96-well plate containing infected BHK cells in paper-supported MATRIGEL™ matrix.

A linear increase in luminescence was observed corresponding to the linear increase in lux-VSV titer (FIG. 12B). Each data point corresponds to the readout from a unique well; dispersion of the readouts from the assays conducted in similar conditions was low. These results demonstrate that quantification and screening for cell responses using luminescence reporter systems can be extended to high-throughput systems.

Example 5—Analysis of PC-12 Cells Grown in MATRIGEL™-Permeated Paper

We analyzed the growth of the PC-12 rat adrenal pheochromocytoma cell line in MATRIGEL™-permeated paper. PC-12 cells are known to undergo neuronal differentiation upon treatment with nerve growth factor (NGF).

Figures 13A, 13B:
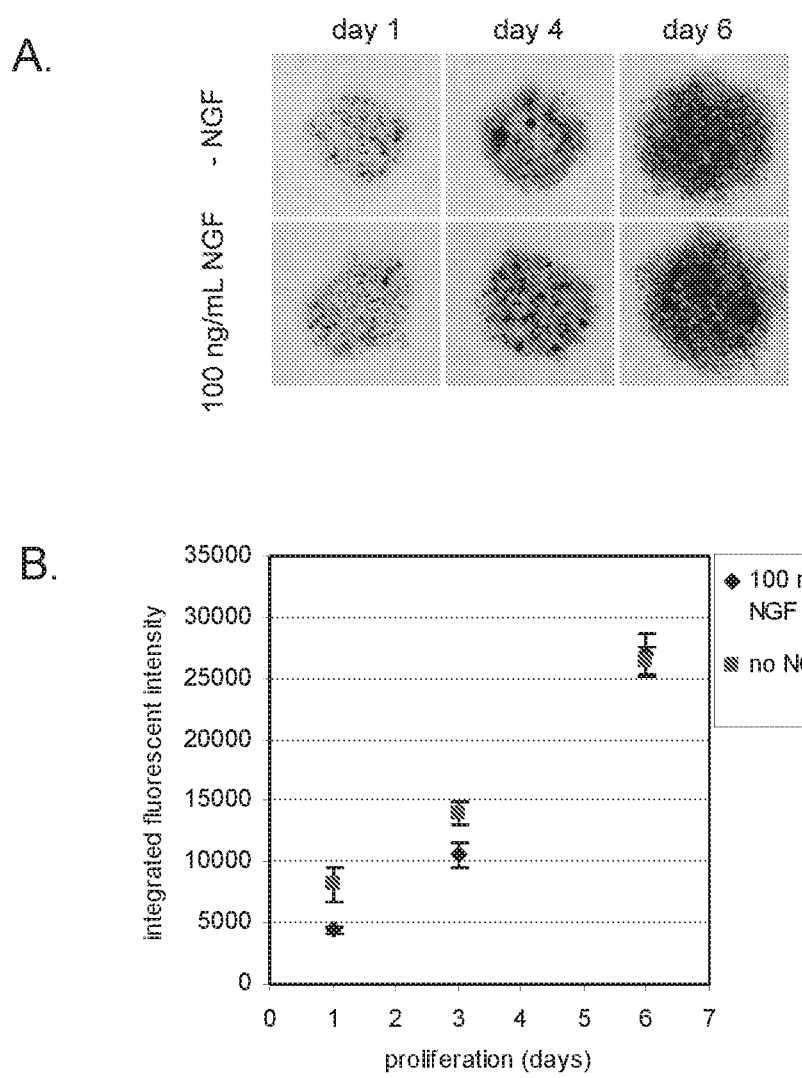
FIG. 13A is a gel scanner image of PC12 cells in MATRIGEL™ spotted onto filter paper and grown under various conditions.
FIG. 13B is a graph of the proliferation of PC12 cells in MATRIGEL™ spotted onto filter paper and grown under various conditions.

First, we assessed the proliferation of PC-12 cells grown in paper in response to NGF. Suspensions of PC12 cells in MATRIGEL™ (1 uL, $5 \times 10^6$ cells/mL) were spotted onto filter paper. The paper was placed in serum-containing media (2.5% fetal bovine serum, 15% horse serum in F12K basal media) or serum-containing media supplemented with 100 ng/mL of nerve growth factor (NGF). Cells within paper MATRIGEL™ matrix were cultured for the indicated times, fixed with formaldehyde, and stained with Alexa Fluor 488-conjugated phalloidin. The paper was scanned using a Typhoon fluorescent gel scanner (see FIG. 13A). The images were quantified using ImageJ software, and an average from 4 measurements is presented in FIG. 13B. Error bars are one standard deviation.

Cells proliferated in paper supported matrix with population doubling time of 36 hours. Moreover, in serum containing media, NGF had little effect on growth rate of the cells.

Next, we assessed whether PC-12 cells maintained in paper-supported three-dimensional matrices were differentiated into neurons using NGF-treatment. We spotted suspensions of PC12 cells in MATRIGEL™ onto paper and suspended the paper in the media supplemented with NGF or with a combination of NGF and the ROCK inhibitor Y27632. Confocal microscopy examination uncovered neuron-like cells with long neurites. The morphology of cells and length of neurites varied when different media/additives were used. For example, after 6 days of culture in the presence of 100 ng/mL NGF, short neurites were developed by cells in serum containing media, longer neurites were developed in serum-free media, and extensive 3D network of interconnected neurites was observed in serum-free media in the presence of 5 µM Y27632 ROCK inhibitor.

Figure 14:
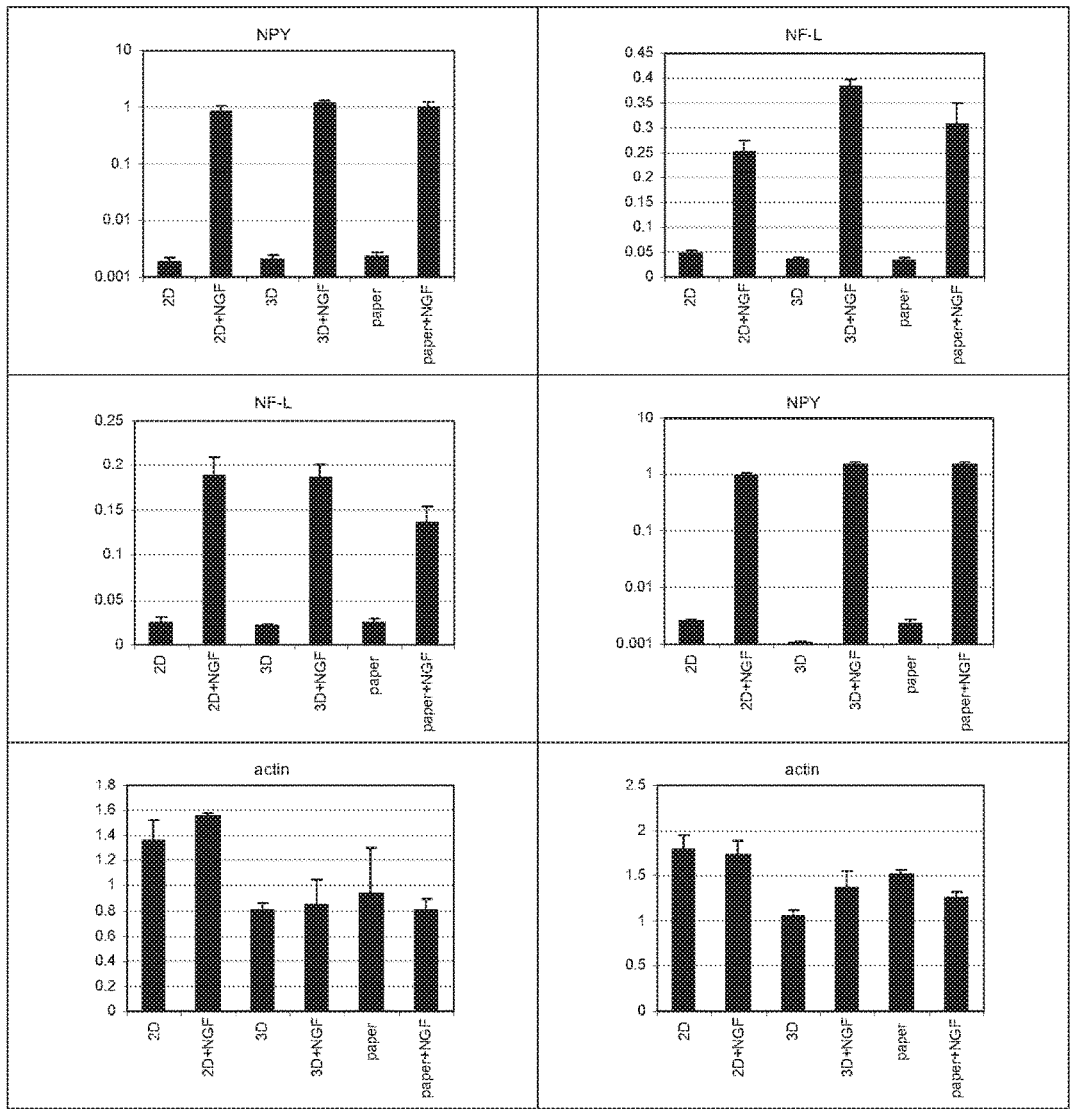
FIG. 14 depicts graphs of quantitative PCR analysis of NGF-induced differentiation of PC12 cells plated on the surfaces coated with a thin layer of MATRIGEL™ ("2D"), suspensions of PC12 cells in MATRIGEL™ allowed to gel to form MATRIGEL™-encapsulated cells ("3D"), or suspensions of PC12 cells in MATRIGEL™ permeated into paper ("paper").

To confirm the observed neuronal phenotype, the cells were analyzed by quantitative PCR and were shown to upregulate the neuron specific neurofilament L (NF-L) and neuropeptide Y (NPY) transcripts (FIG. 14). Finally, we compared the differentiation of PC-12 cells maintained in paper-supported MATRIGEL™ ("paper") with that of cells in paper-free MATRIGEL™ ("3D") or on MATRIGEL™ coated surfaces ("2D").

Cells in these matrices were proliferated in serum-containing media or in media supplemented with 100 ng/mL NFG. On day 3 or 4, the samples were processed to isolate mRNA and the level of expression of NF-L or NPY were assessed by quantitative PCR. GAPDH and actin were used as housekeeping controls. ΔΔCT-analysis was performed in the linear range for every primer using GAPDH as a reference. In FIG. 14, each data point is an average of measurements from 3 independent samples. The error bar is one standard deviation.

We observed no differences in the levels of NF-L and NPY expression induced by NFG-treatment (FIG. 14). This observation suggested that paper does not interfere with the differentiation of these cells and paper-based platforms can be used for screening for agents that modulate differentiation of cells in three-dimensional environments.

Figure 15A:
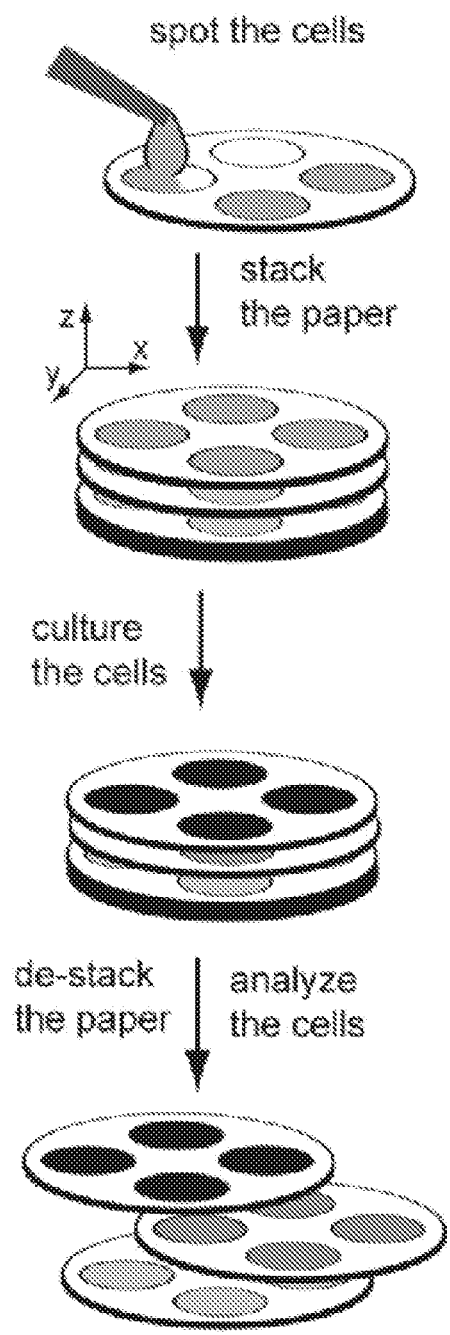
FIG. 15A is a schematic depicting the stacking of multiple layers of paper permeated with suspension of cells in MATRIGEL™ to investigate proliferation of cells in nutrient- and oxygen-limited conditions.

Example 6—Multiple Layers of Paper-supported Hydrogels to Investigate Proliferation of Cells in Nutrient and Oxygen-limited Three-dimensional Cultures Layering of multiple sheets of paper were used to pattern cells in three dimensions and to create complex three-dimensional assemblies of cells. Importantly, the stacked layers were disassembled and the cells in each layer were able to be examined individually (FIG. 15A). Within a multilayer culture, cells in layers at the different depths are exposed to different concentrations of oxygen and nutrients. The multi-layer culture, thus, can be used to investigate the proliferation of different cell types in a gradient of nutrient and oxygen concentration.

To compare the behavior of several cell types in multi-layer cultures, 4 µL of primary cells (HUVECs, HDF, IMR-90) or immortalized cells (HS-5) in MATRIGEL™ were spotted onto 200 µm-thick chromatography paper. The cells were incubated in the appropriate media for 24 hours (allowing the cells to spread) and were stacked onto 6-8 layers of paper. To create a uni-directional gradient of oxygen and nutrients in a stacked layer, an impermeable layer was placed on the bottom of the stack (FIG. 15A). The stacked cells for 7 days (HUVECs) or 9 days (HDF, IMR90, HS-5). The cells were fixed and de-stacked. Cells were stained with Alexa Fluor 633-conjugated phalloidine, imaged using a gel scanner and analyzed using ImageJ. Grey scale intensity corresponding to density of cells on day 1 was set to 1.0; intensities in all layers were normalized to that on day 1. In the analysis the density of cells that proliferated for 9 days in non-stacked paper were included (dark line, FIGS. 15B, 15E, 15F, 15G).

Figures 15B, 15C, 15D:
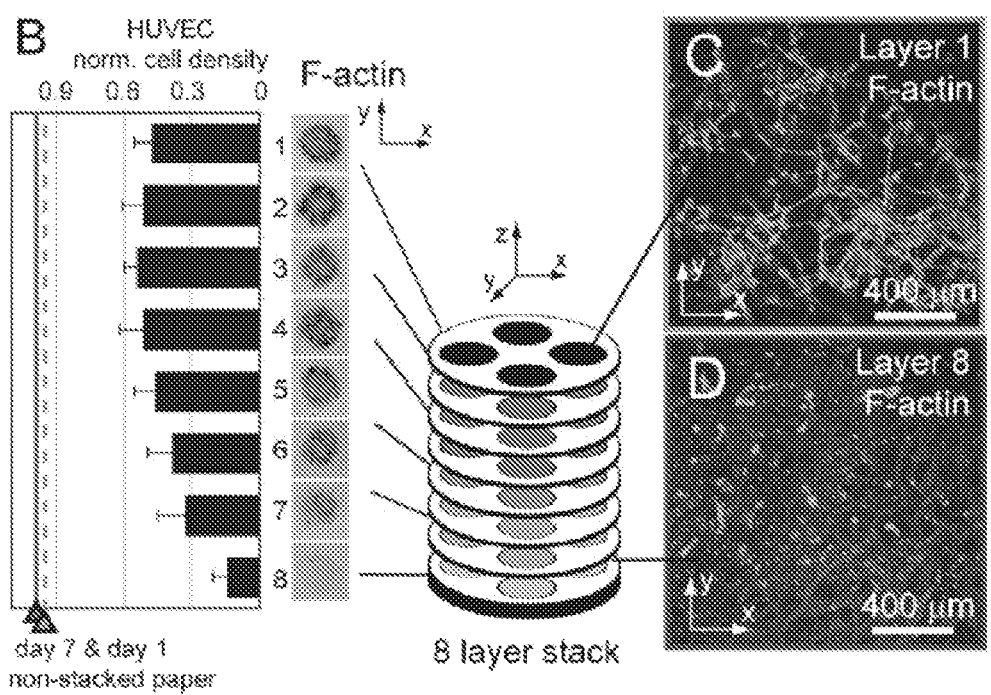
FIG. 15B depicts Scanned images and quantification of cell density in the layers of the 8-layered stack of HUVEC cells after 7 days of culture. Cells were stained with Alexa Fluor 633-conjugated phalloidine, imaged using a gel scanner and analyzed using ImageJ. Grey scale intensities in all layers were normalized to that of cells on day 1. Vertical red line and blue dashed line designates stain intensity of cells in non-stacked layer on day 7 and 1 respectively. All data points are average from 8 measurements and the error bas is equal to one standard deviation.
FIGS. 15C and 15D are confocal images of the network of lumens formed on day 7 in top layer and the small lumens in the bottom layer of the 8-layered stack of HUVECs. Cells were stained with AF488-phalloidin.
Figures 15E, 15F, 15G, 15H:
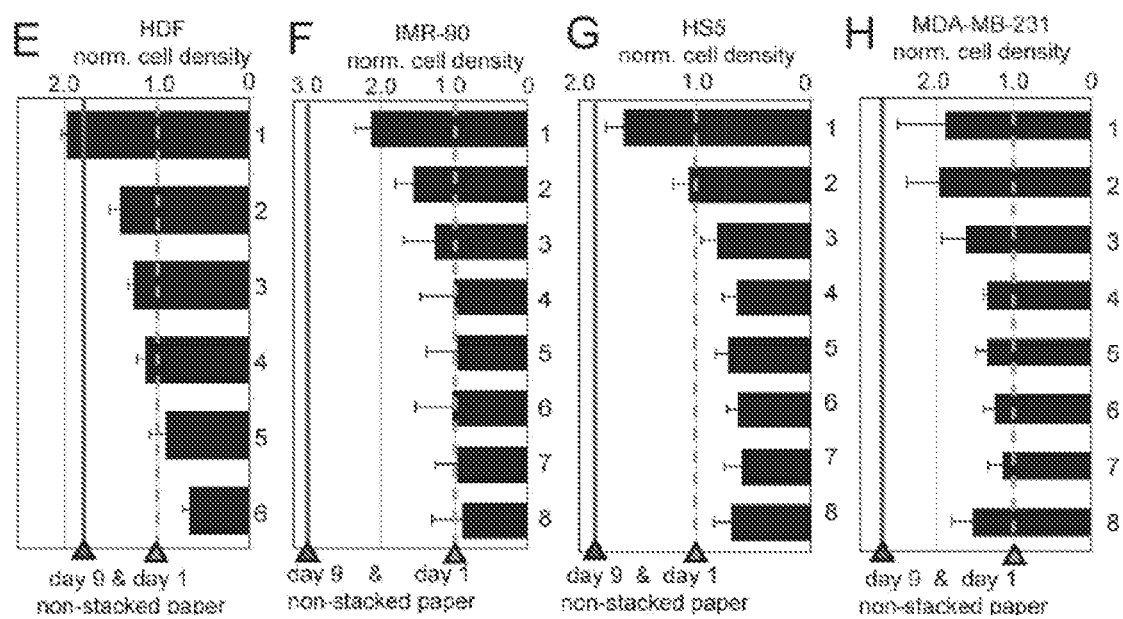
FIG. 15E is a graph of the quantification of cell density in the layers of an 6-layered stack of HDF fibroblasts after 9 days of culture.
FIG. 15F is a graph of the quantification of cell density in the layers of an 8-layered stack of IMR-90 fibroblast cells after 9 days of culture.
FIG. 15G is a graph of the quantification of cell density in the layers of an 8-layered stack of HS-5 bone marrow stroma cells after 9 days of culture.
FIG. 15H is a graph of the quantification of cell density in the layers of an 8-layered stack of MDA-MB-231 after 9 days of culture.

In the HDF and HS-5 stacked cultures, the density of cells in the top layer was similar to that of the cells proliferated for 11 days in the non-stacked paper (FIG. 15B). Hence, even in the unidirectional gradient, cells within 200 µm were exposed to sufficient amounts nutrient and oxygen to support their proliferation.

IMR90 and HUVEC cells exhibited decreased proliferation even in the top layer. We hypothesized that this decrease is due to blocking of the access of nutrients from one side of the paper. In free-floating layer where access of nutrients can occur from either side of the paper and the cells are on average 100 µm or less from the bulk solution. With one side of the paper blocked, the average distance to bulk solution effectively doubles and becomes ~200 µm. This doubling of the thickness might be detrimental for these cell lines that might be more sensitive to oxygen deprivation. In a control experiment, one layer of HUVEC cells was placed on top of 7 layers that contain MATRIGEL™ (without cells) and impermeable layer underneath. This configuration effectively blocks access of nutrient and oxygen from one side of the paper. The number of cells in the top (cell containing) layer was less than that in free-floating layer and it was similar to the number of cells in the top stack of 8 layers of HUVECs (not shown).

Figure 15I:
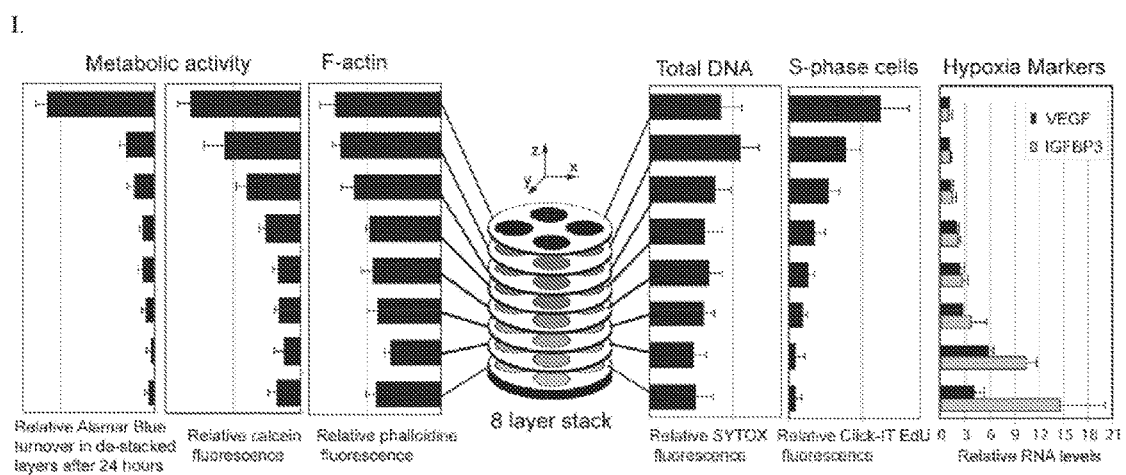
FIG. 15I depicts quantification of metabolic activity (calcein stain), total actin (Texas Red phalloidin stain), total DNA (sytox stain), and total number of proliferating cells (Click-iT EdU® stain), and levels of expression of hypoxic markers (qPCR for VEGF and IGFBP3) in the 8-stack of MDA-MB-231 cells proliferated for 9 days.

In all cases, cell density below the first layer (>200 µm depth) was significantly lower that that in non-stacked layer control (dark line, FIGS. 15B, 15E, 15F, 15G). Comparison with the starting cell density (1.0 grid line, FIGS. 15B, 15E, 15F, 15G) revealed that loss of proliferation occurred at different layers for different cell types. For the tested cell lines the "no-proliferation depths" were: HUVEC—200 µm; HS-5—400 µm, IMR-90—600 µm, HDF—800 µm. Further experiments can be used to account for cell death, resistance to hypoxia, and other factors. Staining for markers of cell proliferation (EdU) or metabolic activity (calcein, Alamar Blue, FIG. 15I) revealed that the number of metabolically active cells or cells that actively synthesize DNA (S-phase cells) is much lower in any stacks but the top stack. The observed "gradient of S-phase cells" and "gradient of metabolically active cells" are much steeped than gradient of total DNA or total actin stain, indicating that most of the cells in the bottom layers are metabolically inactive and non-proliferating. The cells in the bottom stacks also express much higher level of hypoxia-responsive genes as indicated by quantitative PCR for VEGF and IGFBP3 (FIG. 15I).

Confocal imaging revealed distinct morphological changes of cells in stacked layers. Extensive formation of network of hollow lumens occurred in top 5-6 layers (FIG. 15C). Much smaller lumens were observed in the bottom layer (FIG. 15D) and only individual short lumens were observed in the non-stacked control (not shown). Quantification of average number of nuclei per lumen revealed that, on average, 12.6 cells/lumen were observed in lumens in layer 1, 5.5 cells/lumen in layer 8, and 8.0 cells/lumen in non-stacked control. We hypothesize that formation of longer lumens in top stacked layers compared to those in "non-stacked control" is due to nutrient and oxygen deprivation of HUVECs in multi-layer cultures which stimulates autocrine production of factors (VEGF, etc) that stimulates lumen growth.

Figures 16A, 16B, 16C:
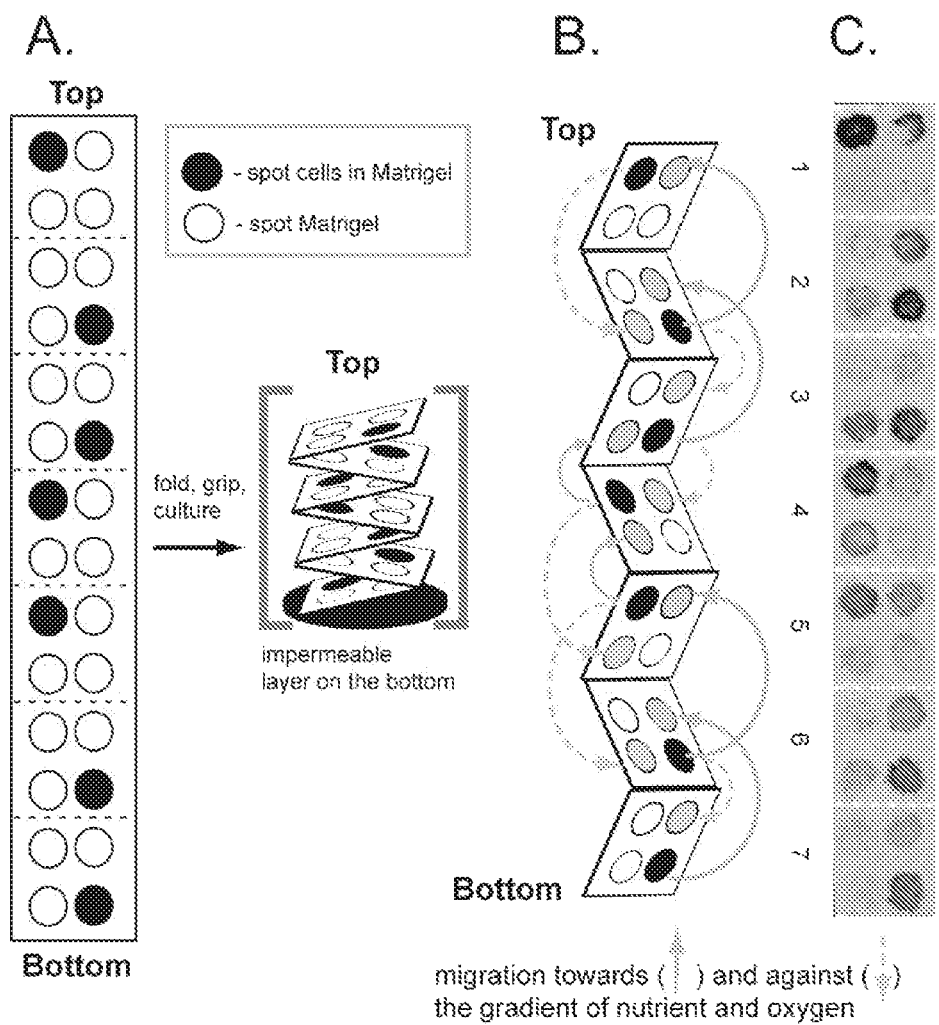
FIG. 16A is a schematic of experiment designed to investigate whether cells can migrate between the layers of MATRIGEL™-permeated paper. suspension of cells in MATRIGEL™ and cell-free MATRIGEL™ are spotted onto a strip of paper. The paper is folded and griped; a sheet of cellulose acetate is placed on the bottom and the stack is cultured for 9 days.
FIG. 16B is a schematic layout of the directions in which the cells can migrate in between the layers. Arrows designate the migration of cells to the adjacent sheets; migration can happen to the overlaying layer which is closer to the bulk media solution (red arrow) or underlying layer which is farther away from bulk media (blue arrow).
FIG. 16C is a representative image of the unfolded paper that contains HDF cells after 9 days of culture. The paper was fixed with formaldehyde, stained with AF647 phalloidine and imaged using fluorescent gel scanner.
Figures 16D, 16E:
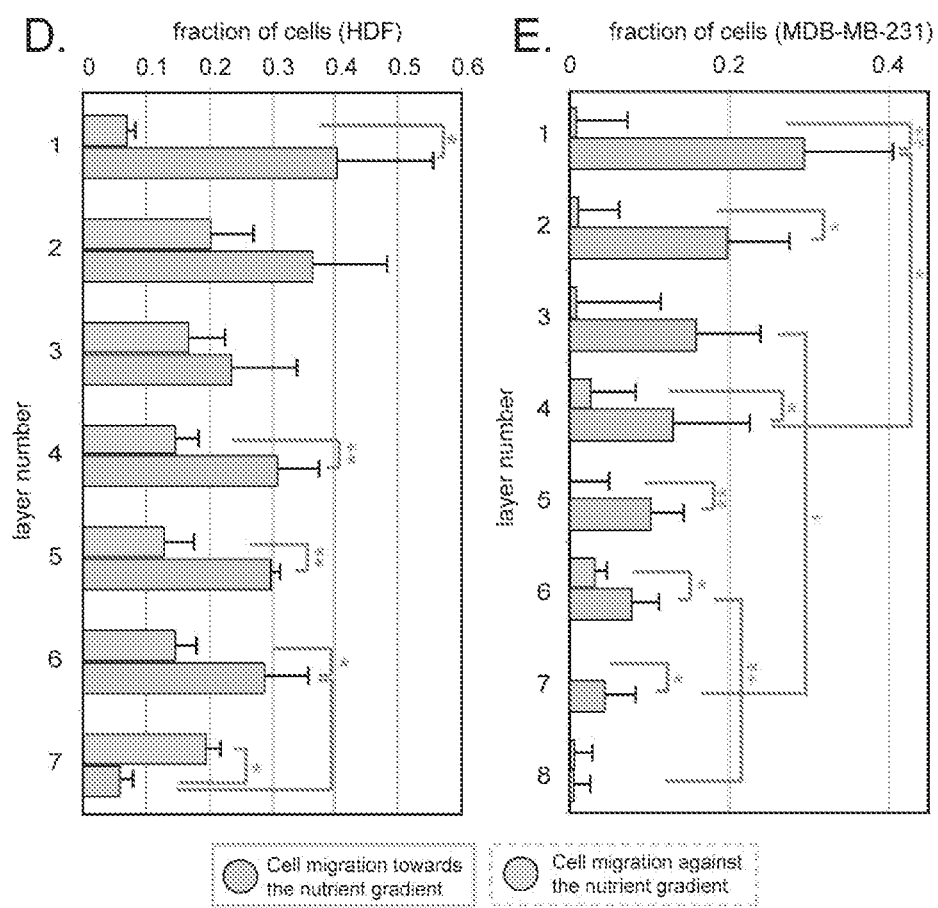
FIG. 16D is a quantitative analysis of HDF cell migration. Migration towards the bulk solution prevails in all layers except the very bottom one. The results are the average from 4 experiments. Error bar is equal to one standard deviation. Two tailed, two sample unequal variance t-test was used to get the p-vaules: * $p<0.05$; ** $p<0.01$.
FIG. 16E is a quantitative analysis of HDF cell migration. Migration towards the bulk solution prevails in all layers except the very bottom one. The results are the average from 5 experiments. Error bar is equal to one standard deviation. * $p<0.05$; ** $p<0.01$.

Example 7—Multiple Layers of Paper-supported Hydrogels to Investigate Migration of Cells in Three-dimensional Cultures Stacking of multiple layers of paper-supported hydrogels were used to investigate three-dimensional migration of cells. Additionally, observation of three-dimensional migration of cells from layer to layer can be used to confirm that a continuous three-dimensional hydrogel is formed upon stacking. A simple way to visualize cell migration is to stack alternating layers that contain cells in paper-supported MATRIGEL™ and layers that contain MATRIGEL™ only. To create this stack, 4 uL of MATRIGEL™ and suspension of cells in MATRIGEL™ were spotted onto the sheet of filter paper. A spotting pattern was selected that upon folding yields a "4-helix" of cell-containing areas surrounded by MATRIGEL™-containing areas. (FIG. 16A). In an effort to enhance the migration of the cells, a unidirectional gradient of nutrients and oxygen was created by placing an impermeable layer (a thin sheet of cellulose acetate) on the bottom of each folded stack (FIG. 16B).

Following nine days of culture, the folded papers were treated with 4% formaldehyde solution, and stained with phalloidin. The stacks were unfolded and the cells were visualized using a gel scanner (FIG. 16C). Cells migrated between the MATRIGEL™-containing sheets. We conclude that each layer is in physical contact with the adjacent layers. Quantification of migration to upper layer vs. lower layer revealed that more cells migrated to upper layer (i.e. along the gradient) to higher concentrations of oxygen and nutrients when compared to cells migrating against the gradient (FIGS. 16D and 16E) To assess the role of conformal contact in migration, we compared behaviors of cells in the layer that were folded and pressed to those that were just folded but were not pressed together. We observed that migration occurred only when the layers were pressed together (not shown). Cells in the layers that are not in conformal contact, hence, can not migrate to adjacent layer.

Example 8—Profiling of Cell Growth and Metabolic Activity in 3D Cultures of Different Geometry We used a paper containing a pattern of holes to create 3D cultures of different geometry (FIG. 18A). The suspension of cells in MATRIGEL™ was permeated into the paper and the paper was stacked and gripped with a stainless steel holder (FIG. 18C). The cells were cultured for 9 days, On day 9, the stacks were incubated with calcein for 30 minutes and then fixed with formaldehyde. The layers were then separated and the calcein intensity was imaged using fluorescent gel scanner. The layers were then stained with Texas Red-conjugated phalloidine and visualized using gel scanner. The results from some 3D geometries are presented in FIGS. 19D and 19E.

Figures 19A, 19B, 19C, 19D, 19E:
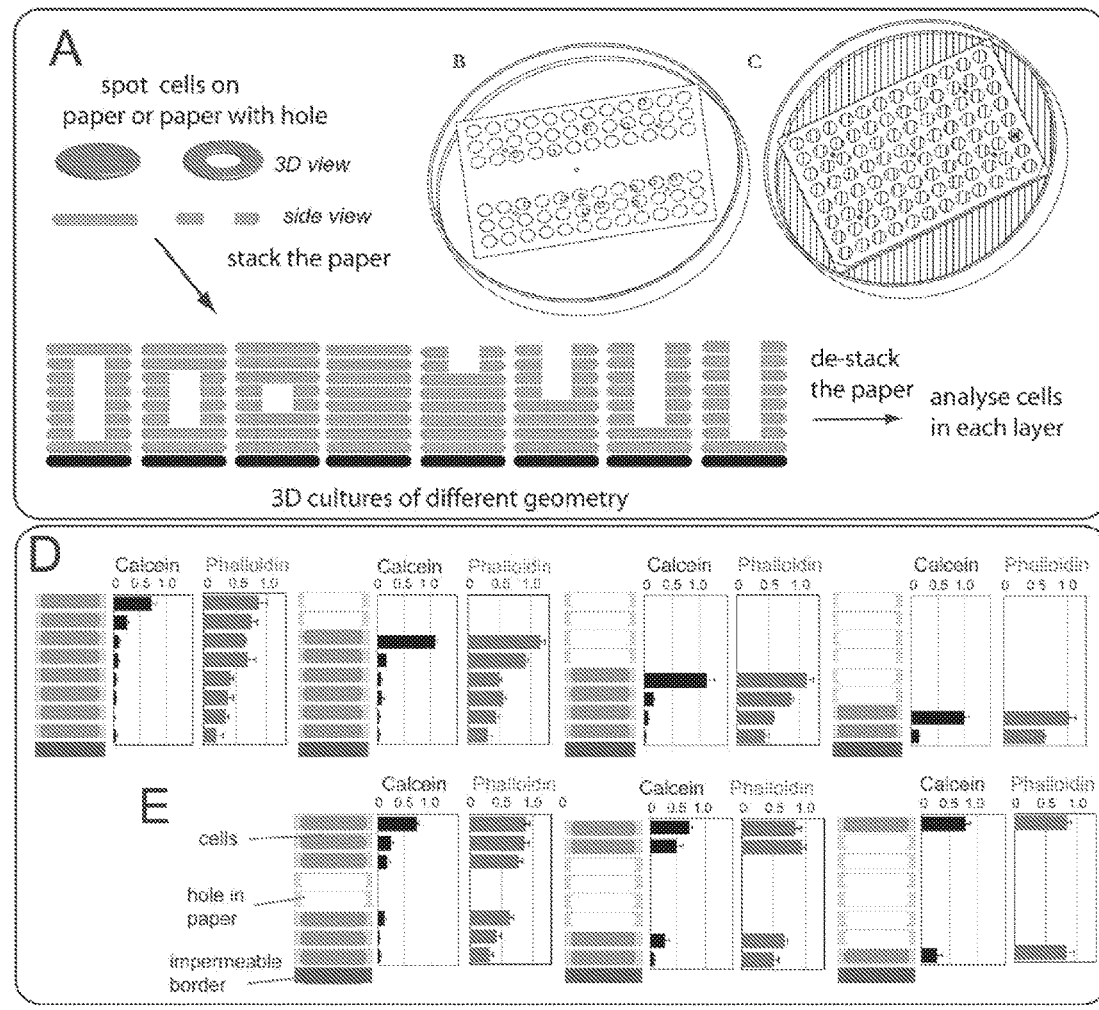
FIG. 19A is a schematic of platform that allows for screening of 3D cultures of different geometry. Stack of perforated papers can be used to create 3D structures with cavities of channels in them.
FIG. 19B is photograph of one of such perforated papers.
FIG. 19C is a photograph of a stack of 8 perforated papers pressed together with a stainless steel holder. Paper-supported cultures in different wells have different 3D geometry.
FIGS. 19D and 19E are the results of one such "geometry screen". Metabolic activity of cells (determined by calcein stain) and total number of cells (measured by actin stain) was investigated in stacks of MDA-MB-231 cells of increasing thickness (FIG. 19D) or increasing "cavity" size (FIG. 19E).

We compared stacks presenting 2, 4, 6 or 8 layers (i.e., 400, 800, 1200 and 1600 micron thick cultures, FIG. 19D) and 3D cultures that have 6, 4 or 2 layers separated by a 2, 4 or 6 layers of "holes in the paper" which effectively creates 400, 800 or 1200 micron gap ("cavity") in the middle of the 3D culture (FIG. 19E). For stacks presenting 8, 6, 4, and 2 layers atop the impermeable border, gradient of metabolic activity is sharply decreasing below layer 1 (FIG. 19D).

Introduction of cavity in 3D cultures increases the overall metabolic activity of cells in the stack and makes cell in the middle of the 3D culture more metabolically active (e.g. compare stack of 4 layers in 18D and the same stack in 18E made of 2+2 layers separated by 800 micron). Because the bottom and the sides of the stack have no access to nutrients and the influx of nutrients and oxygen happens only through the top of the stack, introduction of cavity inside 3D culture does not change effective perfused surface area of the stack (which is on the top). Finally, the number of cells is same or even higher for "separated stacks". Despite these similarities between normal stack and "stack with cavity" the combined metabolic activity is significantly higher in stack with cavity.

Example 9—Multiple Layers of Paper-supported Hydrogels to Investigate the Viability of Bacterial Cells The viability of *Pseudomonas Aeruginosa* strain PA14 cells grown in a stack of 200 micron chromatography paper was investigated. The paper was soaked with a suspension of bacteria, and bacteria were allowed to attach to the paper for several hours. Eight sheets of paper were then stacked (forming an 8-layer stack) and incubated in culture media for 4 hours, 24 hours, or 48 hours. The papers were destacked and the number of dead and live bacteria in each layer were determined using a commercial Live/Dead Bacterial viability Kit, (Invitrogen).

A steady decrease in the number of both live and dead bacteria in the middle of the 8-layered stack was observed. This decrease can be attributable to competing rates of oxygen diffusion and oxygen consumption by bacteria. Although both the top (layer 1) and the bottom (layer 8) of the stack were exposed to media, the media was not stirred, and layer 8 was farthest away from the air/liquid interface. In non-stirred media, there were fewer viable bacteria in layer 8, presumably because less oxygen can access layer 8 compared to layer 1.

Example 10—Development of Sweet Patterning Methods

A. Screening Carbohydrates and Polyols for Ability to Protect Cellulose for Sweet Patterning Methods A screen was developed to identify compounds that can protect cellulose from hydrophobic solutions. Sucrose was initially tested, as sucrose is a cheap and abundant carbohydrate. Solutions of sucrose in various concentrations were spotted onto a filter paper, then a solution of polymer or polymer precursor in hydrophobic solvent was soaked into the paper (see FIG. 2A). Upon polymerization of the precursor or drying of the solvent, the paper was washed with water. Aqueous solutions of Amarant Red were then spotted onto the patterned areas and the beading of the dye droplets provided a qualitative measure of protection. If protection was successful, the spotted areas would remain hydrophilic and they would be subsequently wetted with the aqueous Amarant Red solution. Conversely, in areas where protection was not successful, the polymer-modified paper would be rendered hydrophobic and those areas would not be subsequently wetted with the aqueous Amarant Red solution.

Figures 2B, 2C:
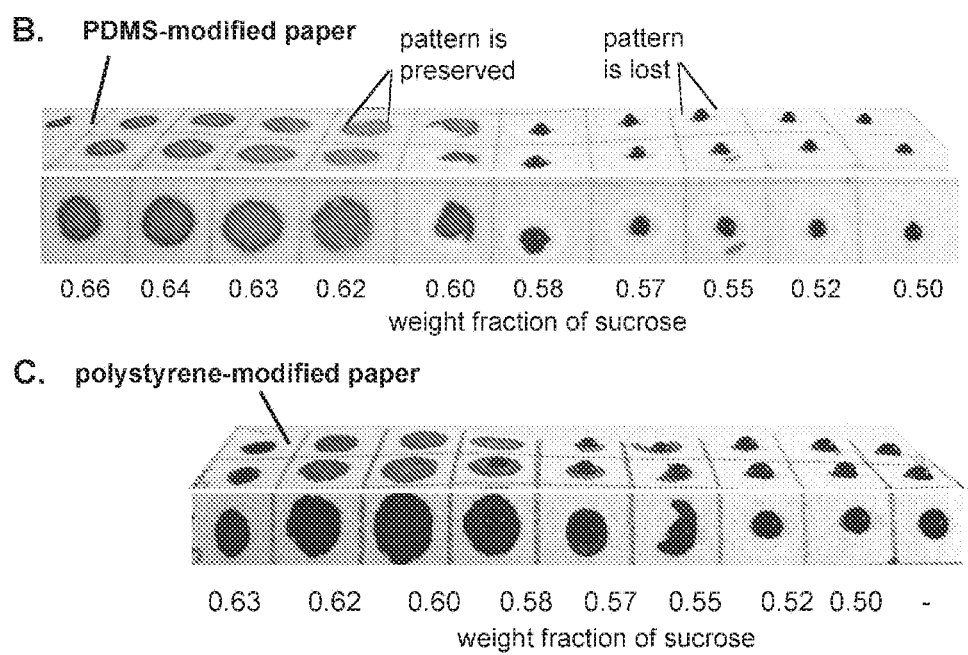
FIG. 2B is a digital representation of papers treated with sucrose, PDMS, then aqueous Amarant Red solution.
FIG. 2C is a digital representation of papers treated with sucrose, polystyrene, then aqueous Amarant Red solution.

To prepare PDMS-modified paper (FIG. 2B), spots of the aqueous solutions of sucrose were deposited onto the paper and the paper was then immersed into solution of PDMS precursors in octane (1:1 wt. mixture). As demonstrated in FIG. 2B, sucrose-protected spots remained hydrophilic, allowing the Amarant Red solution to wet the paper in those sucrose-treated spots. As seen in FIG. 2B, the paper was not protected by low concentration of sucrose (the paper became hydrophobic following PDMS treatment, resulting in the beading of the Amarant Red solution). Similar results were seen using solutions of polystyrene in toluene (FIG. 2C).

Both PDMS and polystyrene formed complementary patterns around the sucrose solutions. Potentially many other types of thermosetting and thermoplastic polymeric materials could be used. These results suggest that any patterns formed by sucrose solutions on the paper can template formation of the complementary hydrophobic patterns within the paper.

Figures 3A, 3B, 3C:
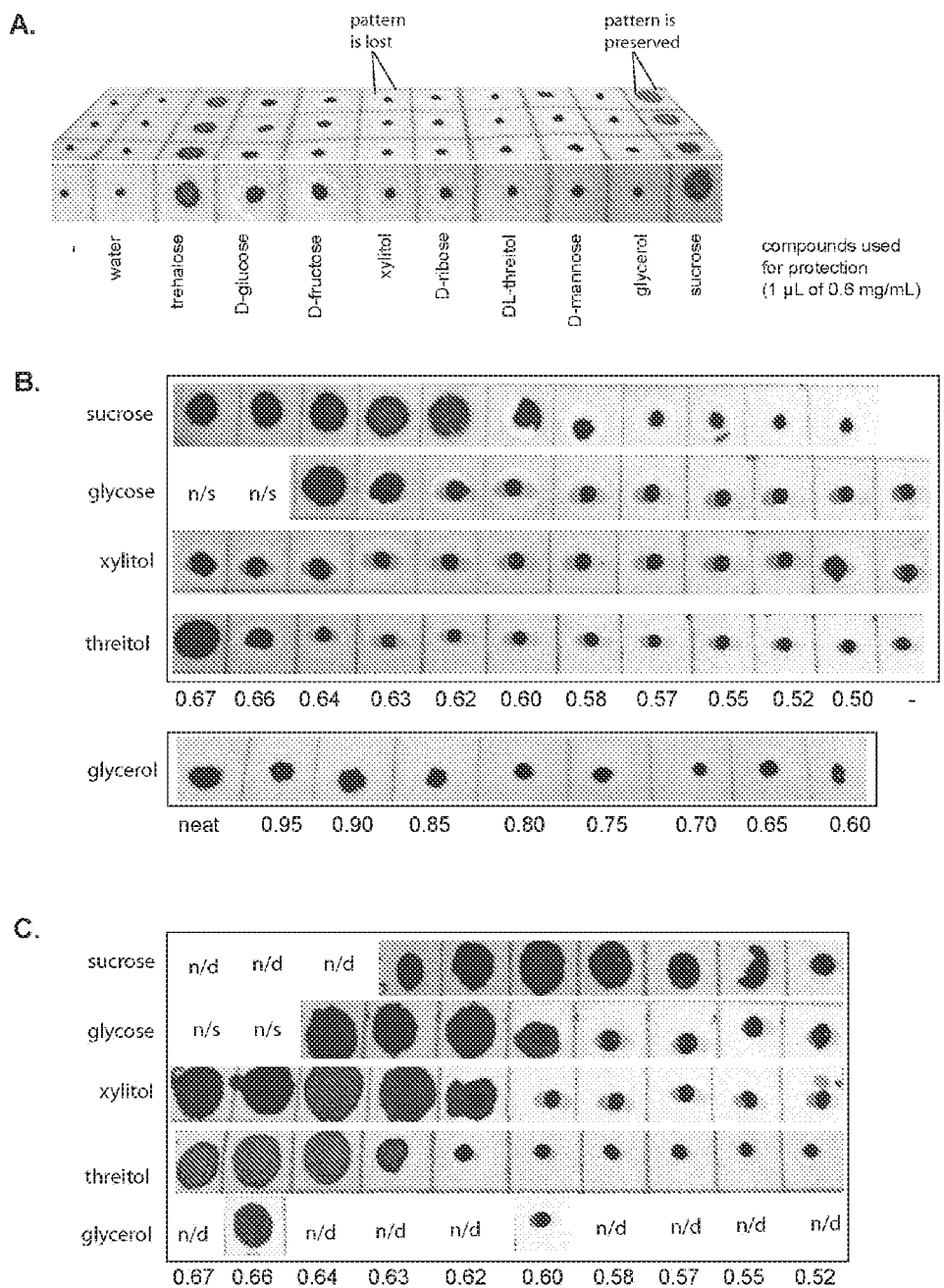
FIG. 3A is a digital representation of papers treated with various compounds, PDMS, then aqueous Amarant Red solution.
FIG. 3B is a digital representation of papers treated with various compounds, PDMS, then aqueous Amarant Red solution.
FIG. 3C is a digital representation of papers treated with various compounds, polystyrene, then aqueous Amarant Red solution. (Abbreviations used: n/s—not soluble; n/d—not determined).

Using the screen outlined in FIG. 2A, cellulose was found to be protected by other carbohydrate derivatives. (See FIG. 3). In FIG. 3A, compounds were dissolved in water (60% weight fraction) and spotted onto filter paper (1 µL drops). Solution of PDMS in n-octane was soaked into the paper. Paper was incubated at 70° C. for 2 h to cure the PDMS and then washed with water. Dye solution (2 µL drops) was used to assess the wetting properties of the spotted regions. In FIG. 3B, various concentrations of different compounds were tested using PDMS as the hydrophobic material. In FIG. 3C, the paper was spotted with listed solutions and immersed briefly into 10 wt. percent solution of polystyrene in toluene. Excess solution was wiped out and the paper was allowed to dry at room temperature.

The protective ability of related compounds was quite different, and the protection of cellulose by carbohydrates and their derivatives was concentration dependent (FIG. 3). Neat glycerol or glycerol-water solutions did not protect cellulose from PDMS. Since evaporation of glycerol is slow compared to the rate of curing of PDMS, the results suggest that glycerol and PDMS-octane solutions are miscible within paper.

The protection profiles against PDMS-octane and polystyrene-toluene varied dramatically (see FIGS. 3B and 3C). The concentration of the compound required for protection was lower for polystyrene than for PDMS. Aqueous glycerol solutions (greater than 60%) protected paper from toluene-polystyrene.

The miscibility of liquids within paper could not be predicted from phase behavior of these liquids in the absence of paper. Some immiscible liquids became miscible within paper (e.g., glycerol and octane-PDMS solution). There was a sharp decline in protection efficiency upon minute changes in concentration for all compounds. The screen described in FIG. 2A provides a method to identify protective compounds and to determine the concentrations for protection.

B. Patterning Using Hydrophilic Solvent, Followed by Spotting by Hydrophilic Solutions If phase-separation is an equilibrium configuration, the order of the addition of solutions should not influence the final state.

Figures 4A, 4B:
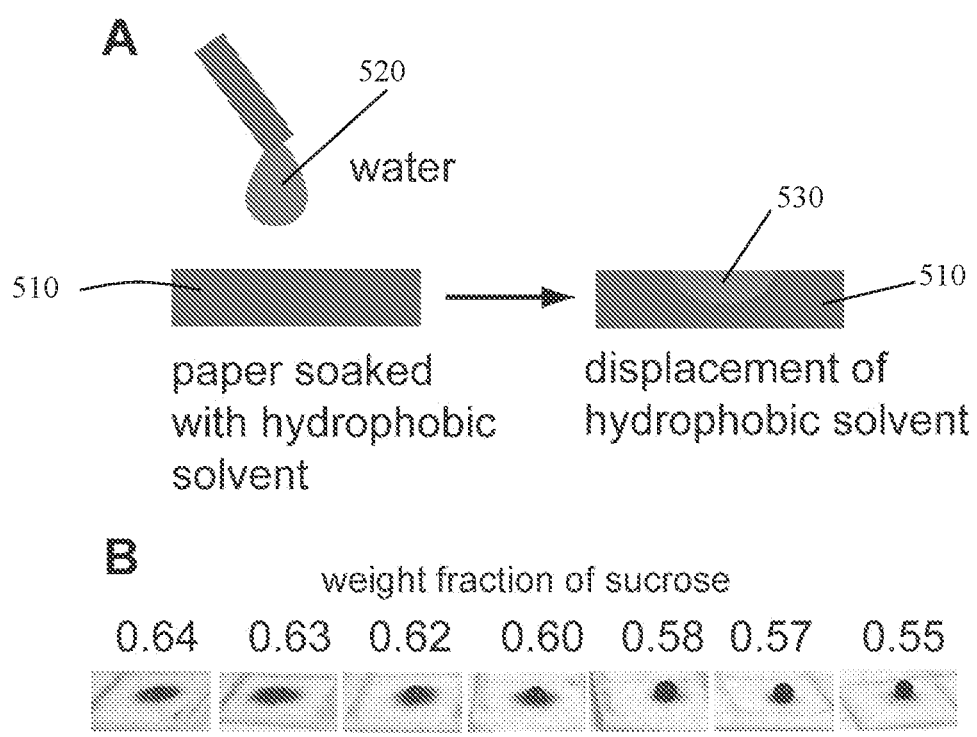
FIG. 4A is a schematic for "sweet patterning".
FIG. 4B is a digital representation of paper treated with PDMS, sucrose, then aqueous Amarant Red solution.

Paper was first soaked in a 1:1 solution of PDMS precursors in n-octane. Solutions of sucrose were spotted onto the PDMS-soaked paper, and the paper was incubated at 70° C. for 2 h to cure the PDMS. Within a few seconds, sucrose drops penetrated into the bulk of the paper and displaced the hydrophobic solution (FIG. 4A). Curing and washing yielded arrays with the same wetting properties as those formed by reversed addition of the reagents (see FIGS. 4B and 2B). Thus, the order of addition of the reagents was not important.

C. Patterning of Paper with Hydrophobic Materials

Figures 5A, 5B, 5C, 5D:
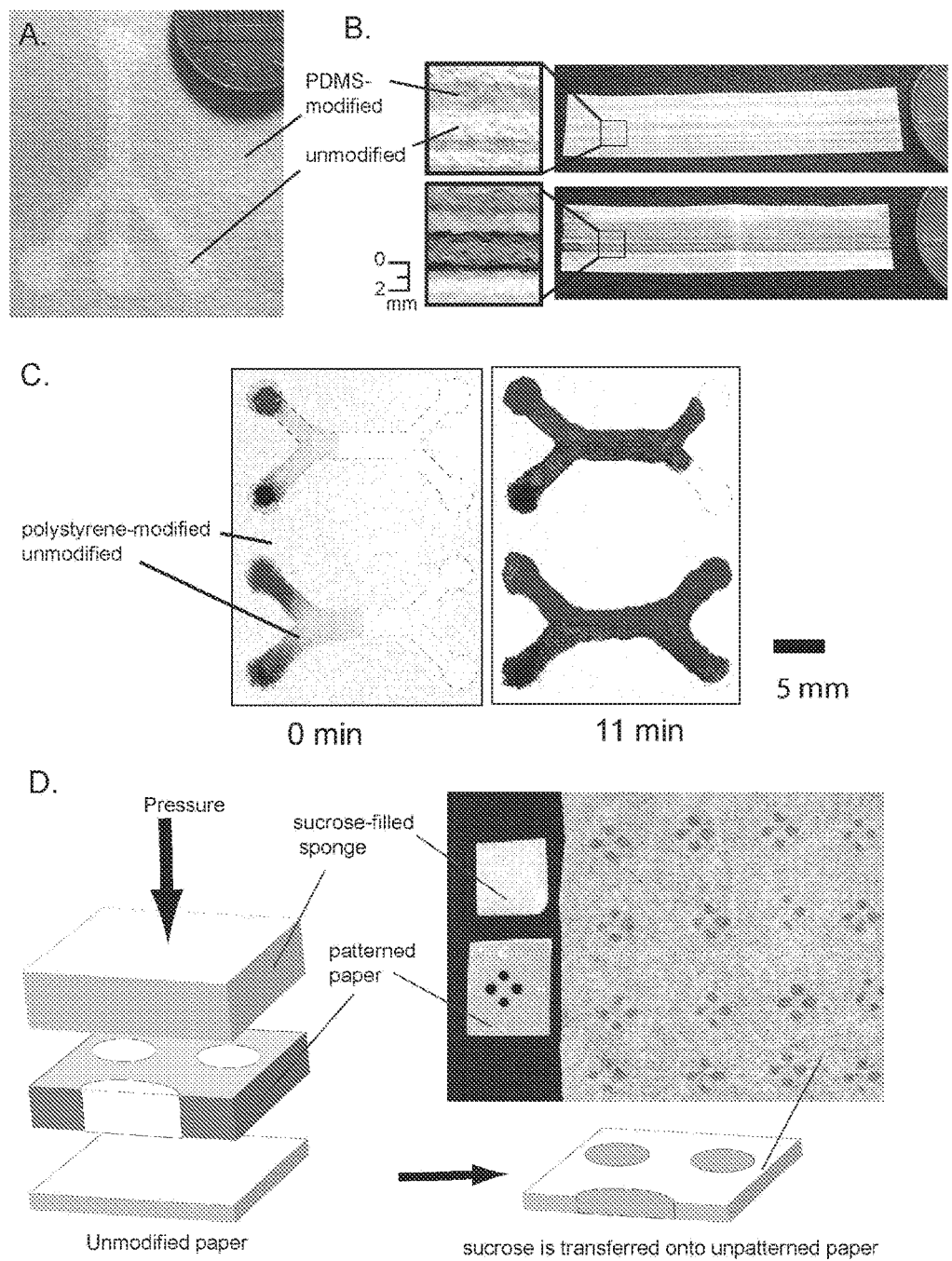
FIGS. 5A and 5B are digital representations of papers patterned with sucrose using an inkjet printer.
FIG. 5C is a digital representation of a paper patterned with sucrose using a fountain pen.
FIG. 5D is a schematic for stamping a sucrose pattern onto paper and a digital representation of a paper patterned with sucrose.

Solutions of sucrose were patterned using many existing techniques for patterning of inks solutions onto the paper. In a first method, patterns were formed using inkjet printing with syrup-filled cartridges (see FIG. 5A). The pattern was printed using an Epson Stylus inkjet printer with syrup-filled cartridge (60 wt % sucrose, 1 wt % glycerol, 0.1% surfanol). Ten consecutive rounds of printing were used to deposit high amount of sucrose, and no loss in resolution was observed; a photograph of a pattern printed as described is shown in FIG. 5A. Printed paper was immersed into 1:1 PDMS-octane solution and cured overnight at 70° C.

Printed patterns remained hydrophilic and could be used for liquid guidance (microfluidics) (see FIG. 5B). 1 mm-wide border between the channels prevented liquid from penetrating into the parallel channel.

In another method, microfluidic channels were formed using a syrup-filled fountain pen (63 wt % solution of sucrose). Dashed outlines of two channels were printed using a conventional laser printer. The outlines were "filled" using a syrup-filled pen. Paper was immersed into polystyrene solution (10 wt % in toluene) and the excess solution was blotted with clean filter paper. The paper was dried at room temperature for 5 minutes and washed with water. Ink solutions (Amarant Red and Coomasie Brilliant blue) were spotted and allowed to wick into the channels. Laminar flow was observed in these channels (FIG. 5C).

In yet another method, patterned paper was fabricated by stamping sucrose solutions onto paper. SU8-patterned paper was used as a basis for the stamp (hydrophilic paper areas are marked with the blue dye). The "stamp" was assembled as shown in FIG. 5D. Syrup-soaked paper, SU8-patterned paper and Kimwipe™ were manually pressed in between two flat surfaces. Stamping was repeated 16 times. Total time required to stamp 16 identical patterns was around 30 seconds. A large number of identical patterns can be rapidly generated using this method.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A cellular system comprising:
a porous, hydrophilic substrate that wicks fluids by capillary action selected from the group consisting of paper, nitrocellulose, cellulose acetate, cloth, and porous polymer film, wherein the substrate comprises at least one porous region, each porous region bounded at least in part by a liquid impervious boundary, and wherein at least one of the porous regions comprises a temperature-sensitive hydrogel comprising cells.

2. The cellular system of claim 1, wherein the liquid impervious boundary is selected from the group consisting of poly(dimethylsiloxane), poly(lactic-co-glycolic acid), epoxy, polystyrene, a polyether, a polyamide, poly(methyl methacrylate), polycarbonate, polyethylene, polypropylene, a photoresist precursors, a wax and a fat and mixtures thereof.

3. The cellular system of claim 1, further comprising:
a bottomless microtiter plate having a plurality of wells disposed over the porous hydrophilic substrate;
wherein the wells of the microtiter plate and the liquid impervious boundaries of the porous hydrophilic substrate are positioned so that the plurality of wells are aligned and sealingly joined to the plurality of liquid impervious boundaries to form an individual chamber for each porous region, wherein the wells and porous regions define an array.

4. A kit comprising:
one or more porous, hydrophilic substrates selected from the group consisting of paper, nitrocellulose, cellulose acetate, cloth, and porous polymer film, wherein the substrate comprises at least one porous region, each porous region bounded at least in part by a liquid impervious boundary; and
a bottomless microtiter plate having a plurality of wells equal to the number of porous regions in the substrate, wherein the wells of the microtiter plate and the liquid impervious boundaries of the porous hydrophilic substrate are positioned so that the plurality of wells are aligned.

5. The kit of claim 4, further comprising a temperature-sensitive hydrogel.

6. A method of making a cellular system, comprising:
providing a porous, hydrophilic substrate selected from the group consisting of paper, nitrocellulose, cellulose acetate, cloth, and porous polymer film, wherein the porous, hydrophilic substrate comprises at least one porous region, each porous region bounded at least in part by a liquid impervious boundary; and
in any order,
contacting a plurality of defined regions of the substrate with a suspension comprising cells and a temperature-sensitive hydrogel precursor, wherein the cells and the hydrogel precursor saturate the plurality of defined regions of the substrate; and
contacting the hydrogel precursor with a gelling agent, wherein the gelling agent induces the formation of a hydrogel embedded in the plurality of defined regions of the substrate.

7. The method of claim 6, wherein cells are introduced into the hydrogel precursor before contacting the hydrogel precursor to the substrate.

8. The method of claim 6, wherein the gelling agent is temperature, a solution containing salt, or a chemical cross-linking agent.

9. The method of claim 6, wherein the liquid impervious boundary is one or more selected from the group consisting of poly(dimethylsiloxane), poly(lactic-co-glycolic acid), epoxy, polystyrene, a polyether, a polyamide, poly(methyl methacrylate), polycarbonate, polyethylene, polypropylene, a photoresist precursors, a wax and a fat and mixtures thereof.

10. The method of claim 6, wherein the cells are one or more cells selected from the group consisting of bacterial cells, insect cells, yeast cells, and mammalian cells.

11. The method of claim 6, further comprising contacting the system with living tissue.

12. A method of identifying an agent that modifies cellular activity, the method comprising:
contacting the cellular system of claim 1 with one or more test agents; and
detecting one or more cellular activities in the presence of the one or more test agents.

13. The method of claim 12, wherein the cellular system is contacted with the one or more test agents at a plurality of defined regions.

14. The method of claim 13, wherein each defined region is contacted with a different test agent.

15. The method of claim 12, wherein the cellular activity is one or more selected from the group consisting of proliferation, migration, apoptosis apoptosis, differentiation, viability, upregulation of gene transcription, or downregulation of gene transcription.

16. The method of claim 12, wherein the test agent is selected from the group consisting of one or more of a small molecule, amino acid, polypeptide, nucleic acid, carbohydrate, polysaccharide, and metabolite.

17. The method of claim 12, wherein the cells are selected from the group consisting of bacterial cells, insect cells, yeast cells, and mammalian cells and mixtures thereof.

18. A method of claim 12, further comprising:
   cutting the cellular system into a plurality of segments, each segment comprising at least one porous region comprising cells and hydrogel;
   contacting each segment with a test agent or a control; and
   detecting one or more cellular activities in the presence of the test agent.

19. The cellular system of claim 1, wherein the cells are one or more cells selected from the group consisting of bacterial cells, insect cells, yeast cells, and mammalian cells and mixtures thereof.

20. The cellular system of claim 1, wherein there are a plurality of porous regions positioned in the porous hydrophilic substrate in the form of an array.

\* \* \* \* \*